(12) United States Patent
van de Ven

(10) Patent No.: US 12,115,384 B2
(45) Date of Patent: Oct. 15, 2024

(54) DEVICES AND METHODS FOR ILLUMINATING TISSUE TO INDUCE BIOLOGICAL EFFECTS

(71) Applicant: KNOW Bio, LLC, Durham, NC (US)

(72) Inventor: Antony Paul van de Ven, Nong Kae (TH)

(73) Assignee: KNOW Bio, LLC, Morrisville, NC (US)

( * ) Notice: Subject to any disclaimer, the term of this patent is extended or adjusted under 35 U.S.C. 154(b) by 185 days.

(21) Appl. No.: 17/201,061

(22) Filed: Mar. 15, 2021

(65) Prior Publication Data

US 2022/0288413 A1    Sep. 15, 2022

(51) Int. Cl.
*A61N 5/06*    (2006.01)

(52) U.S. Cl.
CPC ......... *A61N 5/0603* (2013.01); *A61N 5/0624* (2013.01); *A61N 2005/0606* (2013.01); *A61N 2005/0607* (2013.01)

(58) Field of Classification Search
CPC .............. A61N 5/0603; A61N 5/0624; A61N 2005/0606; A61N 2005/0607; A61N 2005/063; A61N 2005/0652
See application file for complete search history.

(56) References Cited

U.S. PATENT DOCUMENTS

| | | |
|---|---|---|
| 1,244,819 A | 10/1917 | Young |
| 2,884,926 A | 5/1959 | Grasso |
| 4,466,434 A | 8/1984 | Brownstein |
| 4,493,796 A | 1/1985 | Rinehart, Jr. |
| 4,736,745 A | 4/1988 | Gluckman |
| 5,074,295 A | 12/1991 | Willis |
| 5,228,431 A | 7/1993 | Giarretto |
| 5,282,462 A | 2/1994 | Kudo |
| 5,292,346 A | 3/1994 | Ceravolo |
| 5,541,822 A | 7/1996 | Bamber |
| 5,549,639 A | 8/1996 | Ross |
| 5,611,793 A | 3/1997 | Wilson et al. |
| 5,616,140 A | 4/1997 | Prescott |

(Continued)

FOREIGN PATENT DOCUMENTS

| | | |
|---|---|---|
| AU | 2016100390 A4 | 7/2016 |
| CN | 101687101 A | 3/2010 |

(Continued)

OTHER PUBLICATIONS

Notice of Allowance for Brazilian Patent Application No. BR112018001874-0, mailed Aug. 28, 2022, 6 pages.

(Continued)

*Primary Examiner* — Joseph M Dietrich
*Assistant Examiner* — Michael T. Holtzclaw
(74) *Attorney, Agent, or Firm* — Withrow & Terranova, P.L.L.C.

(57) ABSTRACT

An illumination device includes a light source and a deformable light guide optically coupled to the light source. The deformable light guide is configured to conform to a surface of tissue when in contact with the tissue such that light from the light source is coupled directly from the deformable light guide to the tissue. By using a deformable light guide, more light can be delivered to a target tissue. This may increase treatment efficacy, reduce treatment time, or both.

45 Claims, 9 Drawing Sheets

(56) References Cited

U.S. PATENT DOCUMENTS

| | | |
|---|---|---|
| 5,634,711 A | 6/1997 | Kennedy et al. |
| 5,658,148 A | 8/1997 | Neuberger et al. |
| 5,683,436 A | 11/1997 | Mendes et al. |
| 6,026,828 A | 2/2000 | Altshuler |
| 6,045,499 A | 4/2000 | Pitesky |
| 6,096,066 A | 8/2000 | Chen et al. |
| 6,171,332 B1 | 1/2001 | Whitehurst |
| 6,201,764 B1 | 3/2001 | Rice et al. |
| 6,211,626 B1 | 4/2001 | Lys et al. |
| 6,244,865 B1 | 6/2001 | Nelson et al. |
| 6,251,127 B1 | 6/2001 | Biel |
| 6,283,956 B1 | 9/2001 | McDaniel |
| 6,290,496 B1 | 9/2001 | Azar et al. |
| 6,290,713 B1 | 9/2001 | Russell |
| 6,379,376 B1 | 4/2002 | Lubart |
| 6,443,978 B1 | 9/2002 | Zharov |
| 6,462,070 B1 | 10/2002 | Hasan et al. |
| 6,471,716 B1 | 10/2002 | Pecukonis |
| 6,491,618 B1 | 12/2002 | Ganz |
| 6,497,719 B2 | 12/2002 | Pearl et al. |
| 6,551,346 B2 | 4/2003 | Crossley |
| 6,561,808 B2 | 5/2003 | Neuberger |
| 6,623,513 B2 | 9/2003 | Biel |
| 6,645,230 B2 | 11/2003 | Whitehurst |
| 6,663,659 B2 | 12/2003 | McDaniel |
| 6,676,655 B2 | 1/2004 | McDaniel |
| 6,887,260 B1 | 5/2005 | McDaniel |
| 6,890,346 B2 | 5/2005 | Ganz et al. |
| 6,902,397 B2 | 6/2005 | Farrell et al. |
| 6,918,922 B2 | 7/2005 | Oron |
| 6,936,044 B2 | 8/2005 | McDaniel |
| 6,955,684 B2 | 10/2005 | Savage, Jr. et al. |
| 6,977,075 B2 | 12/2005 | Hasan et al. |
| 6,989,023 B2 | 1/2006 | Black |
| 7,090,497 B1 | 8/2006 | Harris |
| 7,107,996 B2 | 9/2006 | Ganz et al. |
| 7,144,248 B2 | 12/2006 | Irwin |
| 7,159,590 B2 | 1/2007 | Rife |
| 7,201,764 B2 | 4/2007 | Pearl et al. |
| 7,201,765 B2 | 4/2007 | McDaniel |
| 7,223,270 B2 | 5/2007 | Altshuler et al. |
| 7,223,281 B2 | 5/2007 | Altshuler et al. |
| 7,226,470 B2 | 6/2007 | Kemeny et al. |
| 7,267,673 B2 | 9/2007 | Pilcher et al. |
| 7,303,578 B2 | 12/2007 | De Taboada et al. |
| 7,304,201 B2 | 12/2007 | Holloway et al. |
| 7,309,348 B2 | 12/2007 | Streeter et al. |
| 7,329,273 B2 | 2/2008 | Altshuler et al. |
| 7,329,274 B2 | 2/2008 | Altshuler et al. |
| 7,422,598 B2 | 9/2008 | Altshuler et al. |
| 7,435,252 B2 | 10/2008 | Krespi et al. |
| 7,467,946 B2 | 12/2008 | Rizoiu et al. |
| 7,494,503 B2 | 2/2009 | McDaniel |
| 7,544,204 B2 | 6/2009 | Krespi et al. |
| D599,954 S | 9/2009 | Michaels et al. |
| 7,763,058 B2 | 7/2010 | Sterenborg et al. |
| D631,604 S | 1/2011 | Michaels et al. |
| D635,686 S | 4/2011 | Tucker et al. |
| 7,918,229 B2 | 4/2011 | Cumbie et al. |
| 7,950,396 B2 | 5/2011 | Rose et al. |
| D639,751 S | 6/2011 | Tucker et al. |
| D640,793 S | 6/2011 | Britt |
| 8,021,148 B2 | 9/2011 | Goodson et al. |
| 8,021,405 B2 | 9/2011 | White |
| 8,025,686 B2 | 9/2011 | Morgan |
| 8,029,278 B1 | 10/2011 | Levine |
| 8,053,977 B2 | 11/2011 | Lifka et al. |
| 8,088,122 B2 | 1/2012 | Li et al. |
| 8,109,981 B2 | 2/2012 | Gertner et al. |
| 8,146,607 B2 | 4/2012 | Rabin et al. |
| 8,186,997 B2 | 5/2012 | Binner et al. |
| 8,192,473 B2 | 6/2012 | Tucker et al. |
| 8,214,958 B2 | 7/2012 | Pinyayev et al. |
| 8,240,312 B2 | 8/2012 | Feuerstein et al. |
| 8,252,033 B2 | 8/2012 | Tucker et al. |
| 8,398,264 B2 | 3/2013 | Anderson et al. |
| 8,435,273 B2 | 5/2013 | Lum et al. |
| 8,486,123 B2 | 7/2013 | Vizethum et al. |
| 8,518,029 B2 | 8/2013 | Birmingham et al. |
| 8,535,361 B2 | 9/2013 | Lim et al. |
| 8,556,951 B2 | 10/2013 | Witt et al. |
| 8,641,702 B2 | 2/2014 | Pilcher et al. |
| 8,651,111 B2 | 2/2014 | McDaniel |
| 8,668,727 B2 | 3/2014 | Natale et al. |
| 8,684,577 B2 | 4/2014 | Vayser |
| 8,685,466 B2 | 4/2014 | Piergallini et al. |
| 8,690,933 B2 | 4/2014 | Mitchell |
| 8,710,460 B2 | 4/2014 | Dayton |
| 8,721,696 B2 | 5/2014 | Krespi et al. |
| 8,747,446 B2 | 6/2014 | Chen et al. |
| 8,758,215 B2 | 6/2014 | Legendre et al. |
| 8,771,327 B2 | 7/2014 | Pearl et al. |
| 8,790,381 B2 | 7/2014 | Pierce |
| 8,815,931 B2 | 8/2014 | Grafe et al. |
| D712,561 S | 9/2014 | Hagenauer |
| 8,838,228 B2 | 9/2014 | Beisang, III et al. |
| 8,845,704 B2 | 9/2014 | Dunning et al. |
| D716,493 S | 10/2014 | Michaels et al. |
| 8,858,607 B1 | 10/2014 | Jones |
| 8,900,282 B2 | 12/2014 | Brawn |
| 8,900,283 B2 | 12/2014 | Johnson et al. |
| 8,940,775 B2 | 1/2015 | Fedele et al. |
| 9,017,391 B2 | 4/2015 | McDaniel |
| 9,039,966 B2 | 5/2015 | Anderson et al. |
| 9,040,103 B2 | 5/2015 | Marrot et al. |
| 9,095,704 B2 | 8/2015 | McGuire |
| 9,132,279 B2 | 9/2015 | Roersma et al. |
| 9,144,690 B2 | 9/2015 | McDaniel |
| 9,149,348 B2 | 10/2015 | Wu et al. |
| 9,162,001 B2 | 10/2015 | Sunkara et al. |
| 9,180,308 B1 | 11/2015 | Frost |
| 9,192,780 B2 | 11/2015 | McDaniel |
| 9,198,502 B2 | 12/2015 | Barnes et al. |
| 9,211,420 B2 | 12/2015 | Patel et al. |
| 9,215,921 B2 | 12/2015 | Thiebaut et al. |
| 9,227,082 B2 | 1/2016 | McDaniel |
| D754,897 S | 4/2016 | Michaels et al. |
| 9,308,389 B2 | 4/2016 | Brawn |
| 9,333,274 B2 | 5/2016 | Peterson et al. |
| 9,415,237 B2 | 8/2016 | Wagenaar Cacciola et al. |
| 9,439,989 B2 | 9/2016 | Lalicki et al. |
| 9,474,811 B2 | 10/2016 | Sharma |
| 9,504,752 B2 | 11/2016 | Kanno et al. |
| 9,504,847 B2 | 11/2016 | Pryor et al. |
| D777,339 S | 1/2017 | Chen |
| 9,545,524 B2 | 1/2017 | Maass et al. |
| 9,554,963 B2 | 1/2017 | Pilcher et al. |
| 9,561,077 B2 | 2/2017 | Alfano |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,700,641 B2 | 7/2017 | Hawkins et al. |
| 9,724,536 B1 | 8/2017 | Rabin et al. |
| 9,730,780 B2 | 8/2017 | Brawn et al. |
| 9,744,375 B2 | 8/2017 | Oberreiter et al. |
| D804,047 S | 11/2017 | Michaels et al. |
| 9,808,646 B2 | 11/2017 | Piergallini et al. |
| 9,808,647 B2 | 11/2017 | Rhodes et al. |
| 9,901,747 B2 | 2/2018 | Gamelin et al. |
| 9,907,976 B2 | 3/2018 | Bourke, Jr. et al. |
| 9,913,994 B2 | 3/2018 | Marchese et al. |
| 10,010,718 B2 | 7/2018 | Basiony |
| 10,220,221 B2 | 3/2019 | Wu |
| 10,258,442 B2 | 4/2019 | Snyder et al. |
| 10,272,262 B2 | 4/2019 | Bourke, Jr. et al. |
| 10,328,276 B2 | 6/2019 | Williams et al. |
| 10,357,661 B2 | 7/2019 | Hellstrom et al. |
| 10,406,379 B2 | 9/2019 | Sentis et al. |
| 10,416,366 B2 | 9/2019 | Rose et al. |
| 10,463,873 B1 | 11/2019 | Yang et al. |
| 10,525,275 B2 | 1/2020 | Stasko et al. |
| 10,561,854 B2 | 2/2020 | Kim et al. |
| 10,569,097 B2 | 2/2020 | Medendorp, Jr. et al. |
| 10,639,498 B2 | 5/2020 | Enwemeka et al. |

(56) References Cited

U.S. PATENT DOCUMENTS

| | | |
|---|---|---|
| 10,682,203 B2 | 6/2020 | Vazales |
| 10,729,524 B2 | 8/2020 | Brawn et al. |
| 10,780,189 B2 | 9/2020 | Randers-Pehrson et al. |
| 10,981,017 B2 | 4/2021 | Enwemeka et al. |
| 11,058,888 B1 | 7/2021 | Steier et al. |
| 11,147,984 B2 | 10/2021 | Emerson et al. |
| 11,266,855 B2 | 3/2022 | Enwemeka et al. |
| 11,318,325 B2 | 5/2022 | Rezaie et al. |
| 2002/0029071 A1 | 3/2002 | Whitehurst |
| 2002/0128648 A1 | 9/2002 | Weber et al. |
| 2002/0135763 A1 | 9/2002 | MacKinnon et al. |
| 2002/0151941 A1 | 10/2002 | Okawa et al. |
| 2002/0173833 A1 | 11/2002 | Korman et al. |
| 2003/0009205 A1* | 1/2003 | Biel ............ A61N 5/0601 607/88 |
| 2003/0023284 A1 | 1/2003 | Gartstein et al. |
| 2003/0045778 A1 | 3/2003 | Ohline et al. |
| 2003/0076281 A1 | 4/2003 | Morgan et al. |
| 2003/0130709 A1 | 7/2003 | D.C. et al. |
| 2003/0153825 A1 | 8/2003 | Mooradian et al. |
| 2003/0167080 A1 | 9/2003 | Hart et al. |
| 2003/0233138 A1 | 12/2003 | Spooner |
| 2003/0236487 A1 | 12/2003 | Knowlton |
| 2004/0032750 A1 | 2/2004 | Watts et al. |
| 2004/0039242 A1 | 2/2004 | Tolkoff et al. |
| 2004/0044384 A1 | 3/2004 | Leber et al. |
| 2004/0052798 A1 | 3/2004 | Neuberger |
| 2004/0073079 A1 | 4/2004 | Altshuler et al. |
| 2004/0073278 A1 | 4/2004 | Pachys |
| 2004/0162596 A1 | 8/2004 | Altshuler et al. |
| 2004/0193235 A1 | 9/2004 | Altshuler et al. |
| 2004/0193236 A1* | 9/2004 | Altshuler ............ A61B 18/203 607/88 |
| 2004/0199227 A1 | 10/2004 | Altshuler et al. |
| 2005/0024853 A1* | 2/2005 | Thomas-Benedict ........................ A61N 5/0619 362/103 |
| 2005/0045189 A1 | 3/2005 | Jay |
| 2005/0055070 A1 | 3/2005 | Jones et al. |
| 2005/0059731 A1 | 3/2005 | Albrecht et al. |
| 2005/0064371 A1 | 3/2005 | Soukos et al. |
| 2005/0107853 A1 | 5/2005 | Krespi et al. |
| 2005/0231983 A1 | 10/2005 | Dahm |
| 2005/0256553 A1 | 11/2005 | Strisower |
| 2006/0019220 A1 | 1/2006 | Loebel et al. |
| 2006/0085052 A1 | 4/2006 | Feuerstein et al. |
| 2006/0093561 A1 | 5/2006 | Kennedy |
| 2006/0167531 A1 | 7/2006 | Gertner et al. |
| 2006/0183071 A1 | 8/2006 | Hsueh |
| 2006/0194164 A1 | 8/2006 | Altshuler et al. |
| 2006/0239921 A1 | 10/2006 | Mangat et al. |
| 2006/0258896 A1 | 11/2006 | Haber et al. |
| 2006/0287696 A1 | 12/2006 | Wright et al. |
| 2007/0038272 A1 | 2/2007 | Liu |
| 2007/0060819 A1 | 3/2007 | Altshuler et al. |
| 2007/0099154 A1 | 5/2007 | Johnson |
| 2007/0100254 A1 | 5/2007 | Murakami et al. |
| 2007/0105063 A1 | 5/2007 | Pinyayev et al. |
| 2007/0106856 A1 | 5/2007 | Nomura et al. |
| 2007/0135874 A1 | 6/2007 | Bala |
| 2007/0149868 A1 | 6/2007 | Blank et al. |
| 2007/0185553 A1 | 8/2007 | Kennedy |
| 2007/0208396 A1 | 9/2007 | Whatcott et al. |
| 2007/0213792 A1 | 9/2007 | Yaroslavsky et al. |
| 2007/0219600 A1 | 9/2007 | Gertner et al. |
| 2007/0233208 A1 | 10/2007 | Kurtz et al. |
| 2007/0259310 A1 | 11/2007 | Goodson et al. |
| 2007/0260231 A1 | 11/2007 | Rose et al. |
| 2007/0270650 A1 | 11/2007 | Eno et al. |
| 2008/0021370 A1 | 1/2008 | Bornstein |
| 2008/0032252 A1 | 2/2008 | Hayman et al. |
| 2008/0033516 A1 | 2/2008 | Altshuler et al. |
| 2008/0038685 A1 | 2/2008 | Sakaguchi et al. |
| 2008/0065175 A1 | 3/2008 | Redmond et al. |
| 2008/0096156 A1 | 4/2008 | Rose et al. |
| 2008/0097414 A1 | 4/2008 | Li et al. |
| 2008/0145813 A1 | 6/2008 | Crohn |
| 2008/0161748 A1 | 7/2008 | Tolkoff et al. |
| 2008/0210233 A1 | 9/2008 | McCarthy |
| 2008/0214530 A1 | 9/2008 | Colles |
| 2008/0245371 A1 | 10/2008 | Gruber |
| 2008/0254405 A1 | 10/2008 | Montgomery et al. |
| 2008/0269849 A1 | 10/2008 | Lewis |
| 2008/0280260 A1 | 11/2008 | Belikov et al. |
| 2008/0319430 A1 | 12/2008 | Zenzie et al. |
| 2009/0035725 A1 | 2/2009 | Loebel et al. |
| 2009/0093865 A1 | 4/2009 | Krespi et al. |
| 2009/0132011 A1 | 5/2009 | Altshuler et al. |
| 2009/0143842 A1 | 6/2009 | Cumbie et al. |
| 2009/0148808 A1 | 6/2009 | Alexander et al. |
| 2009/0254156 A1 | 10/2009 | Powell et al. |
| 2009/0318802 A1 | 12/2009 | Boyden et al. |
| 2009/0323370 A1 | 12/2009 | Koo |
| 2010/0004645 A1 | 1/2010 | Jeong et al. |
| 2010/0042040 A1 | 2/2010 | Arentz |
| 2010/0049180 A1 | 2/2010 | Wells et al. |
| 2010/0063565 A1 | 3/2010 | Beerwerth et al. |
| 2010/0076526 A1 | 3/2010 | Krespi et al. |
| 2010/0076529 A1 | 3/2010 | Tucker et al. |
| 2010/0106077 A1 | 4/2010 | Rabin et al. |
| 2010/0121131 A1 | 5/2010 | Mathes |
| 2010/0136646 A1 | 6/2010 | Tsen et al. |
| 2010/0160838 A1 | 6/2010 | Krespi |
| 2010/0204762 A1 | 8/2010 | De Taboada et al. |
| 2010/0222852 A1 | 9/2010 | Vasily et al. |
| 2010/0239998 A1 | 9/2010 | Snyder et al. |
| 2010/0242155 A1 | 9/2010 | Carullo, Jr. |
| 2010/0286673 A1 | 11/2010 | Altshuler et al. |
| 2010/0331928 A1 | 12/2010 | Dunning et al. |
| 2011/0015707 A1 | 1/2011 | Tucker et al. |
| 2011/0020173 A1 | 1/2011 | Pryor et al. |
| 2011/0054573 A1 | 3/2011 | Mitchell |
| 2011/0054574 A1 | 3/2011 | Felix |
| 2011/0125229 A1 | 5/2011 | Lytle et al. |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0162155 A1 | 7/2011 | Wai |
| 2011/0215261 A1 | 9/2011 | Lyslo et al. |
| 2011/0264174 A1 | 10/2011 | McNeill et al. |
| 2011/0301673 A1 | 12/2011 | Hoffer et al. |
| 2012/0045738 A1 | 2/2012 | Ho et al. |
| 2012/0059440 A1 | 3/2012 | Hamid |
| 2012/0065709 A1 | 3/2012 | Dunning et al. |
| 2012/0088204 A1 | 4/2012 | Ho et al. |
| 2012/0096657 A1 | 4/2012 | So et al. |
| 2012/0126134 A1 | 5/2012 | Deal et al. |
| 2012/0191162 A1 | 7/2012 | Villa |
| 2012/0209359 A1 | 8/2012 | Chen et al. |
| 2012/0215292 A1 | 8/2012 | Gustavsson |
| 2012/0223216 A1 | 9/2012 | Flaherty et al. |
| 2012/0263625 A1 | 10/2012 | Aicher et al. |
| 2012/0270183 A1 | 10/2012 | Patel et al. |
| 2012/0310307 A1 | 12/2012 | Zhou |
| 2012/0322018 A1 | 12/2012 | Lowe et al. |
| 2013/0006119 A1 | 1/2013 | Pan et al. |
| 2013/0041432 A1 | 2/2013 | Tucker et al. |
| 2013/0089829 A1 | 4/2013 | Boutoussov et al. |
| 2013/0103120 A1* | 4/2013 | Salteri ............ A61K 33/00 424/617 |
| 2013/0131762 A1 | 5/2013 | Oversluizen et al. |
| 2013/0144364 A1 | 6/2013 | Wagenaar Cacciola et al. |
| 2013/0158358 A1 | 6/2013 | Holland |
| 2013/0172959 A1 | 7/2013 | Azoulay |
| 2013/0196284 A1 | 8/2013 | Brawn |
| 2013/0197495 A1 | 8/2013 | Koifman et al. |
| 2013/0245417 A1 | 9/2013 | Spector |
| 2013/0280671 A1 | 10/2013 | Brawn et al. |
| 2014/0023983 A1 | 1/2014 | Lowe et al. |
| 2014/0067024 A1 | 3/2014 | Jones et al. |
| 2014/0128941 A1 | 5/2014 | Williams |
| 2014/0128942 A1 | 5/2014 | Bembridge et al. |
| 2014/0148879 A1 | 5/2014 | Mersch |
| 2014/0163218 A1 | 6/2014 | Dei et al. |

(56) References Cited

U.S. PATENT DOCUMENTS

| | | |
|---|---|---|
| 2014/0171926 A1 | 6/2014 | Depfenhart |
| 2014/0194955 A1 | 7/2014 | Povolosky et al. |
| 2014/0243933 A1 | 8/2014 | Ginggen |
| 2014/0267662 A1 | 9/2014 | Lampo |
| 2014/0276247 A1 | 9/2014 | Hall et al. |
| 2014/0276248 A1 | 9/2014 | Hall et al. |
| 2014/0288351 A1 | 9/2014 | Jones |
| 2014/0296524 A1 | 10/2014 | Jones et al. |
| 2014/0303693 A1 | 10/2014 | Haarlander et al. |
| 2014/0323946 A1 | 10/2014 | Bourke, Jr. et al. |
| 2014/0350643 A1 | 11/2014 | Pepitone et al. |
| 2015/0005854 A1 | 1/2015 | Said |
| 2015/0030989 A1 | 1/2015 | Soukos et al. |
| 2015/0045720 A1 | 2/2015 | Kanno et al. |
| 2015/0112411 A1 | 4/2015 | Beckman et al. |
| 2015/0164618 A1 | 6/2015 | Heacock et al. |
| 2015/0217130 A1 | 8/2015 | Gross et al. |
| 2015/0265353 A1 | 9/2015 | Andrews et al. |
| 2015/0297914 A1 | 10/2015 | Hamid et al. |
| 2016/0000214 A1 | 1/2016 | Kim |
| 2016/0015840 A1 | 1/2016 | Gordon |
| 2016/0016001 A1 | 1/2016 | Loupis et al. |
| 2016/0039854 A1 | 2/2016 | McFarland |
| 2016/0051835 A1 | 2/2016 | Tapper et al. |
| 2016/0059031 A1 | 3/2016 | Wescott et al. |
| 2016/0106999 A1 | 4/2016 | Michaels et al. |
| 2016/0114185 A1 | 4/2016 | Mankin |
| 2016/0129278 A1 | 5/2016 | Mayer |
| 2016/0151639 A1 | 6/2016 | Scharf et al. |
| 2016/0271415 A1 | 9/2016 | Min |
| 2016/0271420 A1 | 9/2016 | Pina |
| 2016/0317832 A1 | 11/2016 | Barneck et al. |
| 2017/0027432 A1 | 2/2017 | Wachs |
| 2017/0028215 A1 | 2/2017 | Medendorp, Jr. et al. |
| 2017/0028216 A1 | 2/2017 | Medendorp, Jr. et al. |
| 2017/0165499 A1 | 6/2017 | Blanche et al. |
| 2017/0173358 A1 | 6/2017 | Demarest et al. |
| 2017/0203132 A1 | 7/2017 | Luttrull et al. |
| 2017/0224206 A1 | 8/2017 | Vayser |
| 2017/0225011 A1 | 8/2017 | Frost |
| 2017/0290648 A1 | 10/2017 | Kuo |
| 2017/0333728 A1 | 11/2017 | Sentis et al. |
| 2017/0340898 A1 | 11/2017 | Moor et al. |
| 2018/0008847 A1 | 1/2018 | Key |
| 2018/0014777 A1 | 1/2018 | Amir et al. |
| 2018/0036554 A1 | 2/2018 | Krespi |
| 2018/0111003 A1 | 4/2018 | Hewitson |
| 2018/0117355 A1 | 5/2018 | Loupis et al. |
| 2018/0146520 A1 | 5/2018 | Williams |
| 2018/0178027 A1 | 6/2018 | Shang |
| 2018/0256916 A1 | 9/2018 | Kothari et al. |
| 2018/0264282 A1 | 9/2018 | Bornstein |
| 2018/0289940 A1 | 10/2018 | Spotnitz et al. |
| 2019/0014901 A1 | 1/2019 | Xi et al. |
| 2019/0030359 A1 | 1/2019 | Dijkstra et al. |
| 2019/0124888 A1 | 5/2019 | Coyle |
| 2019/0134419 A1 | 5/2019 | Bourke Jr. et al. |
| 2019/0142516 A1 | 5/2019 | Boutoussov et al. |
| 2019/0175938 A1 | 6/2019 | Rezaie et al. |
| 2019/0201711 A1 | 7/2019 | Brawn et al. |
| 2019/0209857 A1 | 7/2019 | Brawn et al. |
| 2020/0101315 A1 | 4/2020 | Reinhardt |
| 2020/0114171 A1 | 4/2020 | Tortora |
| 2020/0155350 A1 | 5/2020 | Neev |
| 2020/0222714 A1 | 7/2020 | Stasko et al. |
| 2020/0261608 A1* | 8/2020 | Crosby ............... A61L 2/0047 |
| 2020/0298014 A1 | 9/2020 | Stasko et al. |
| 2020/0298016 A1 | 9/2020 | Yoon et al. |
| 2020/0330186 A1 | 10/2020 | Barros et al. |
| 2020/0353112 A1 | 11/2020 | Randers-Pehrson et al. |
| 2020/0360124 A1 | 11/2020 | Woo et al. |
| 2021/0008384 A1 | 1/2021 | Lee |
| 2021/0128935 A1 | 5/2021 | Stasko et al. |
| 2021/0128936 A1 | 5/2021 | Stasko et al. |
| 2021/0128937 A1 | 5/2021 | Stasko et al. |
| 2021/0128938 A1 | 5/2021 | Stasko et al. |
| 2021/0138259 A1 | 5/2021 | Stasko et al. |
| 2021/0138260 A1 | 5/2021 | Park et al. |
| 2021/0196977 A1 | 7/2021 | Zhang |
| 2021/0205487 A1 | 7/2021 | Balme et al. |
| 2021/0228900 A1 | 7/2021 | Kothari et al. |
| 2021/0260398 A1 | 8/2021 | Bilston et al. |
| 2021/0267738 A1 | 9/2021 | Mackie |
| 2021/0283490 A1 | 9/2021 | Lin |
| 2021/0290970 A1 | 9/2021 | Hunter et al. |
| 2021/0290971 A1 | 9/2021 | Cockrell et al. |
| 2021/0290975 A1 | 9/2021 | Hunter et al. |
| 2021/0346500 A1 | 11/2021 | Schikora |
| 2021/0379400 A1 | 12/2021 | Emerson et al. |
| 2021/0402212 A1 | 12/2021 | Schupp et al. |
| 2022/0023660 A1 | 1/2022 | Emerson et al. |
| 2022/0040495 A1* | 2/2022 | Hwang ............... A61N 5/0603 |
| 2022/0088409 A1 | 3/2022 | Dombrowski et al. |
| 2022/0168586 A1 | 6/2022 | Kothari et al. |
| 2022/0189342 A1 | 6/2022 | Emerson et al. |
| 2022/0226667 A1 | 7/2022 | Kothari et al. |
| 2023/0149735 A1 | 5/2023 | Miskin |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 102731405 A | 10/2012 |
| CN | 102802694 A | 11/2012 |
| CN | 103143015 A | 6/2013 |
| CN | 203169848 U | 9/2013 |
| CN | 103601727 A | 2/2014 |
| CN | 103610464 A | 3/2014 |
| CN | 103724356 A | 4/2014 |
| CN | 103930162 A | 7/2014 |
| CN | 104667432 A | 6/2015 |
| CN | 105664367 A | 6/2016 |
| CN | 108371756 A | 8/2018 |
| DE | 102010010763 A1 | 9/2011 |
| DE | 102013202122 A1 | 6/2014 |
| DE | 102012224183 A1 | 7/2014 |
| EP | 2368598 A1 | 9/2011 |
| EP | 2508229 A1 | 10/2012 |
| EP | 3069762 A1 | 9/2016 |
| EP | 3108931 A1 | 12/2016 |
| GB | 2499921 A | 9/2013 |
| KR | 20100124083 A | 11/2010 |
| KR | 20120090317 A | 8/2012 |
| KR | 101349157 B1 | 1/2014 |
| KR | 20140014689 A | 2/2014 |
| KR | 20190063041 A | 6/2019 |
| WO | 1995010243 A1 | 4/1995 |
| WO | 2004033040 A1 | 4/2004 |
| WO | 2004084752 A2 | 10/2004 |
| WO | 2006047868 A1 | 5/2006 |
| WO | 2006063318 A1 | 6/2006 |
| WO | 2006130340 A2 | 12/2006 |
| WO | 2008024414 A1 | 2/2008 |
| WO | 2008041296 A1 | 4/2008 |
| WO | 2008051918 A2 | 5/2008 |
| WO | 2008066943 A2 | 6/2008 |
| WO | 2008131343 A1 | 10/2008 |
| WO | 2008144157 A1 | 11/2008 |
| WO | 2009047669 A2 | 4/2009 |
| WO | 2010098761 A1 | 9/2010 |
| WO | 2011083378 A1 | 7/2011 |
| WO | 2011083381 A1 | 7/2011 |
| WO | 2012001194 A1 | 1/2012 |
| WO | 2013036558 A1 | 3/2013 |
| WO | 2014021557 A1 | 2/2014 |
| WO | 2014089552 A1 | 6/2014 |
| WO | 2014116659 A1 | 7/2014 |
| WO | 2014136255 A1 | 9/2014 |
| WO | 2014146029 A1 | 9/2014 |
| WO | 2015006309 A1 | 1/2015 |
| WO | 2015134204 A1 | 9/2015 |
| WO | 2016039812 A1 | 3/2016 |
| WO | 2016078603 A1 | 5/2016 |

(56) References Cited

FOREIGN PATENT DOCUMENTS

| | | | |
|---|---|---|---|
| WO | 2016081594 A1 | 5/2016 | |
| WO | 2016116859 A1 | 7/2016 | |
| WO | 2016178472 A1 | 11/2016 | |
| WO | 2017019836 A1 | 2/2017 | |
| WO | 2017044931 A1 | 3/2017 | |
| WO | 2017070155 A1 | 4/2017 | |
| WO | 2018026892 A1 | 2/2018 | |
| WO | 2019022275 A1 | 1/2019 | |
| WO | 2019127427 A1 | 7/2019 | |
| WO | 2019145519 A1 | 8/2019 | |
| WO | 2019156921 A1 | 8/2019 | |
| WO | 2019191820 A1 | 10/2019 | |
| WO | 2019234308 A1 | 12/2019 | |
| WO | 2020006048 A1 | 1/2020 | |
| WO | 2020047659 A1 | 3/2020 | |
| WO | 2020081910 A1 | 4/2020 | |
| WO | WO-2021178655 A1 * | 9/2021 | ........... A61N 5/0603 |

OTHER PUBLICATIONS

Corrected Notice of Allowability for U.S. Appl. No. 16/709,550, mailed Sep. 21, 2022, 5 pages.
Non-Final Office Action for U.S. Appl. No. 17/148,124, mailed Oct. 13, 2022, 21 pages.
Final Office Action for U.S. Appl. No. 17/410,154, mailed Oct. 11, 2022, 20 pages.
Non-Final Office Action for U.S. Appl. No. 17/410,166, mailed Oct. 18, 2022, 11 pages.
Final Office Action for U.S. Appl. No. 17/162,259, mailed Oct. 19, 2022, 19 pages.
Non-Final Office Action for U.S. Appl. No. 17/162,283, mailed Nov. 8, 2022, 12 pages.
Non-Final Office Action for U.S. Appl. No. 17/173,457, mailed Oct. 17, 2022, 15 pages.
Zein, Randa, et al., "Review of light parameters and photobiomodulation efficacy: dive into complexity," Journal of Biomedical Optics, vol. 23, Issue 12, Dec. 2018, 17 pages.
Zupin, Luisa, et al., "Antiviral properties of blue laser in an in vitro model of HSV-1 infection," Microbial Immunal, Letter to the Editor, vol. 62, 2018, pp. 477-479.
Zupin, Luisa, et al., "Photobiomodulation therapy reduces viral load and cell death in ZIKV-infected glioblastoma cell line," Lasers in Medical Science, vol. 33, Jul. 2018, Springer Nature, pp. 2011-2013.
International Search Report and Written Opinion for PCT/US2016/044400, mailed Oct. 4, 2016, 8 pages.
International Preliminary Report on Patentability for PCT/US2016/044400, mailed Feb. 8, 2018, 7 pages.
Non-Final Office Action for U.S. Appl. No. 15/222,199, mailed Jan. 11, 2019, 9 pages.
Non-Final Office Action for U.S. Appl. No. 15/222,243, mailed Jan. 11, 2019, 10 pages.
International Preliminary Report on Patentability for PCT/US2016/044403, mailed Feb. 8, 2018, 7 pages.
Final Office Action for U.S. Appl. No. 15/222,199, mailed Jul. 29, 2019, 9 pages.
Notice of Allowance and Applicant-Initiated Interview Summary for U.S. Appl. No. 15/222,199, mailed Sep. 18, 2019, 11 pages.
Final Office Action for U.S. Appl. No. 15/222,243, mailed Jul. 29, 2019, 12 pages.
Notice of Allowance and Applicant-Initiated Interview Summary for U.S. Appl. No. 15/222,243, mailed Dec. 19, 2019, 11 pages.
Non-Final Office Action for U.S. Appl. No. 16/709,550, mailed Apr. 30, 2020, 13 pages.
Hamblin, Michael, "Mechanisms of Low Level Light Therapy," Aug. 14, 2008, 22 pages, photobiology.info/Hamblin.html.
Hamblin, Michael R., "The Role of Nitric Oxide in Low Level Light Therapy," Proceedings of SPIE, vol. 6846, 2008, pp. 684602-1 to 684602-14.
Hessling, Martin, et al., "Selection of parameters for thermal coronavirus inactivation—a data-based recommendation," GMS Hygiene and Infection Control, vol. 15, 2020, 7 pages.
Horby, Peter, et al., "Dexamethasone in Hospitalized Patients with Covid-19—Preliminary Report," New England Journal of Medicine, Jul. 17, 2020, 11 pages.
Jackson, George, et al., "Prevalidation of an Acute Inhalation Toxicity Test Using the EpiAirway In Vitro Human Airway Model," Applied In Vitro Toxicology, vol. 4, Issue 2, 2018, Mary Ann Liebert, Inc., pp. 149-158.
Jensen, Caleb, et al., "Is it Time to Start Transitioning From 2D to 3D Cell Culture," Frontiers in Molecular Biosciences, Review, vol. 7, Mar. 2020, 15 pages.
Jin, Jin, et al., "Noncanonical NF-KB Pathway Controls the Production of Type I Interferons in Antiviral Innate Immunity," Immunity, vol. 40, Mar. 2014, Elsevier Inc., pp. 342-354.
Karu, Tiina I., "Low-Power Laser Therapy," Biomedical Photonics Handbook, Chapter 48, CRC Press, 2003, pp. 48-1 to 48-25.
Kelm, Malte, "Nitric oxide metabolism and breakdown," Review, Biochimica et Biophysica Acta, vol. 1411, 1999, Elsevier Science B.V., pp. 273-289.
Kingsley, David, et al., "Oxygen-dependent laser inactivation of murine norovirus using visible light lasers," Virology Journal, Jul. 31, 2018, 8 pages.
Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.
Kitchel, Elaine, "The Effects of Blue Light on Ocular Health," Journal of Visual Impairment and Blindness, Jun. 2000, AFB, pp. 399-403.
Klein, Eili, et al., "The frequency of influenza and bacterial coinfection: a systematic review and meta-analysis," Influenza and Other Respiratory Viruses, vol. 10, Issue 5, May 2016, John Wiley & Sons Ltd., pp. 394-403.
Kovacs, Izabella et al., "Nitric oxide-based protein modification: formation and site-specificity of protein S-nitrosylation," Frontiers in Plant Science, vol. 4, Article 137, May 14, 2013, 10 pages.
Leong, Mimi, "Effects of Light-Emitting Diode Photostimulation on Burn Wound Healing," Thesis, The University of Texas Graduate School of Biomedical Sciences at Galveston, May 2006, 92 pages.
Li, Jie, et al., "Involvement of the Toll-Like Receptor/Nitric Oxide Signaling Pathway in the Pathogenesis of Cervical Cancer Caused by High-Risk Human Papillomavirus Infection," Biomed Research International, 2017, Hindawi, 9 pages.
Lubart, et al., "A Possible Mechanism for the Bactericidal Effect of Visible Light," Review Article, Laser Therapy, vol. 20, 2011, pp. 17-22.
Mandel, Arkady, et al., "A renaissance in low-level laser (light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Marullo, Rosella, et al., "HPV16 E6 and E7 proteins induce a chronic oxidative stress response via NOX2 that causes genomic instability and increased susceptibility to DNA damage in head and neck cancer cells," Carcinogenesis, vol. 36, Issue 11, 2015, Oxford University Press, pp. 1397-1406.
Moseley, Harry, et al., "Population reference intervals for minimal erythemal doses in monochromator phototesting," Photodermatology, Photoimmunology & Photomedicine, vol. 25, 2009, pp. 8-11.
Narita, Kouji, et al., "Chronic irradiation with 222-nm UVC light induces neither DNA damage nor epidermal lesions in mouse skin, even at high doses," Research Article, PLOS One, doi.org/10.1371/journal.pone.0201259, Jul. 25, 2018, 9 pages.
Narita, Kouji, et al., "Disinfection and healing effects of 222-nm UVC light on methicillin-resistant *Staphylococcus aureus* infection in mouse wounds," Dissertation, Hirosaki University Graduate School of Medicine, 2017, Elsevier, 36 pages.

(56) References Cited

OTHER PUBLICATIONS

Narita, Kouji, et al., "Ultraviolet C light with wavelength of 222 nm inactivates a wide spectrum of microbial pathogens," Journal of Hospital Infection, vol. 105, Mar. 31, 2020, Elsevier Ltd., pp. 459-467.

Perdiz, Daniel, et al., "Distribution and Repair of Bipyrimidine Photoproducts in Solar UV-irradiated Mammalian Cells," Journal of Biological Chemistry, vol. 275, Issue 35, Sep. 2000, pp. 26732-26742.

Pfeifer, Gerd, et al., "UV wavelength-dependent DNA damage and human non-melanoma and melanoma skin cancer," Author Manuscript, Journal of Photochemistry and Photobiology, vol. 11, Issue 1, Jan. 2012, 14 pages.

Phurrough, Steve et al., "Decision Memo for Infrared Therapy Devices (CAG-00291N)," Centers for Medicare & Medicaid Services, Oct. 24, 2006, 37 pages.

Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.

Ramakrishnan, Praveen, et al., "Cytotoxic responses to 405 nm light exposure in mammalian and bacterial cells: Involvement of reactive oxygen species," Toxicology in Vitro, vol. 33, Feb. 2016, Elsevier B.V., pp. 54-62.

Ravanant, Jean-Luc, et al., "Direct and indirect effects of UV radiation on DNA and its components," Journal of Photochemistry and Photobiology, vol. 63, 2001, pp. 88-102.

Richardson, Tobias, et al., "Inactivation of murine leukaemia virus by exposure to visible light," Virology, vol. 341, 2005, Elsevier Inc., pp. 321-329.

Sabino, Caetano, et al., "Light-based technologies for management of COVID-19 pandemic crisis," Journal of Photochemistry and Photobiology, Aug. 2020, Elsevier B.V., 8 pages.

Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.

Saura, Marta, et al., "An Antiviral Mechanism of Nitric Oxide: Inhibition of a Viral Protease," Immunity, vol. 10, Jan. 1999, Cell Press, 8 pages.

Serrage, Hannah, et al., "Under the spotlight: mechanisms of photobiomodulation concentrating on blue and green light," Photochemical and Photobiological Sciences, Jun. 2019, 43 pages.

St. Denis, Tyler, et al., "Killing Bacterial Spores with Blue Light: When Innate Resistance Meets the Power of Light," Photochemistry and Photobiology, vol. 89, Issue 1, Sep. 2012, Wiley Preiodicals, Inc., 7 pages.

Tomb, Rachael, et al., "Inactivation of Streptomyces phage φC31 by 405 nm light," Bacteriophage, vol. 4, Jul. 2014, Landes Bioscience, 7 pages.

Tomb, Rachael, et al., "New Proof-of-Concept in Viral Inactivation: Virucidal Efficacy of 405 nm Light Against Feline Calicivirus as a Model for Norovirus Decontamination," Food Environ Virol, Dec. 2016, pp. 159-167.

Tomoroni, et al., "A Novel Laser Fiberscope for Simultaneous Imaging and Phototherapy of Peripheral Lung Cancer," Chest, vol. 156, Issue 3, Sep. 2019, 8 pages.

Tsen, KT, et al., "Inactivation of viruses by coherent excitations with a low power visible femtosecond laser," Virology Journal, Jun. 2007, BioMed Central Ltd., 5 pages.

Tsen, Shaw-Wei, et al., "Chemical-free inactivated whole influenza virus vaccine prepared by ultrashort pulsed laser treatment," Journal of Biomedical Optics, vol. 20, Issue 5, May 2015, 8 pages.

Tsen, Shaw-Wei, et al., "Inactivation of enveloped virus by laser-driven protein aggregation," Journal of Biomedical Optics, vol. 17, Issue 12, Dec. 2012, 8 pages.

Tsen, Shaw-Wei, "Pathogen Reduction in Human Plasma Using an Ultrashort Pulsed Laser," PLOS One, vol. 9, Issue 11, Nov. 2014, 8 pages.

Tsen, Shaw-Wei, et al., "Prospects for a novel ultrashort pulsed laser technology for pathogen inactivation," Journal of Biomedical Science, Jul. 2012, 11 pages.

Tsen, Shaw-Wei, et al., "Studies of inactivation mechanism of non-enveloped icosahedral virus by a visible ultrashort pulsed laser," Virology Journal, vol. 11, Issue 20, Feb. 2014, BioMed Central Ltd., 9 pages.

Vatansever, Fatma, et al., "Antimicrobial strategies centered around reactive oxygen species—bactericidal antibiotics, photodynamic therapy, and beyond," FEMS Microbiology Reviews, vol. 37, Issue 6, 2013, pp. 955-989.

Wei, Xue-Min, et al., "Relationship between nitric oxide in cervical microenvironment and different HPV types and effect on cervical cancer cells," Zhonghua Fu Chan Ke Za Zhi, vol. 46, Issue 4, Apr. 2011, pp. 260-265 (Abstract Only).

Williams, Vonetta, et al., "Human Papillomavirus Type 16 E6* Induces Oxidative Stress and DNA Damage," Journal of Virology, vol. 88, Issue 12, Jun. 2014, pp. 6751-6761.

Willoughby, Jamin, "Predicting Respiratory Toxicity Using a Human 3D Airway (EpiAirway) Model Combined with Multiple Parametric Analysis," Applied In Vitro Toxicology, vol. 1, Issue 1, 2015, pp. 55-65.

Wolf, Yuri, et al., "Origins and Evolution of the Global RNA Virome," mBio, vol. 9, Issue 6, Nov. 2018, 31 pages.

Ahmed, Imran, et al., "Recent Patents on Light-Based Anti-Infective Approaches," Author Manuscript, Recent Patents on Anti-Infective Drug Discovery, vol. 13, Issue 1, 2018, 28 pages.

Akaberi, Dario, et al., "Mitigation of the replication of SARS-COV-2 by nitric oxide in vitro," Redox Biology, vol. 37, Sep. 21, 2020, Elsevier B.V., 5 pages.

Author Unknown, "Assessing COVID-19-Related Symptoms in Outpatient Adult and Adolescent Subjects in Clinical Trials of Drugs and Biological Products for Covid-19 Prevention or Treatment," Guidance for Industry, US Department of Health and Human Services, Sep. 2020, 14 pages.

Baric, Ralph, "Emergence of a Highly Fit SARS-CoV-2 Variant," New England Journal of Medicine, vol. 383, Issue 27, Dec. 31, 2020, pp. 2684-2686.

Fajnzylber, Jesse, et al., "SARS-CoV-2 viral load is associated with increased disease severity and mortality," Nature Communications, vol. 11, Issue 1, Oct. 30, 2020, 9 pages.

Hamblin, Michael, "Mechanisms and Mitochondrial Redox Signaling in Photobiomodulation," Author Manuscript, Photochemistry and Photobiology, vol. 94, Issue 2, Mar. 2018, 31 pages.

Huang, Ni, et al., "Integrated Single-Cell Atlases Reveal an Oral SARS-CoV-2 Infection and Transmission Axis," medrXiv, Oct. 29, 2020, 22 pages.

Kim, Peter, et al., "Therapy for Early COVID-19: A Critical Need," JAMA, vol. 324, Issue 21, Nov. 11, 2020, American Medical Association, pp. 2149-2150.

Quirk, Brendan, et al., "What Lies at the Heart of Photobiomodulation: Light, Cytochrome C Oxidase, and Nitric Oxide—Review of the Evidence," Photobiomodulation, Photomedicine, and Laser Surgery, vol. 38, Issue 9, Jul. 2020, pp. 527-530.

To, KK, et al., "Temporal profiles of viral load in posterior oropharyngeal saliva samples and serum antibody responses during infection by Sars-CoV-2: an observational cohort study," Lancet Infectious Diseases, vol. 20, Issue 5, Mar. 23, 2020, 11 pages.

Wyllie, Anne, et al., "Saliva or nasopharyngeal swab specimens for detection of SARS-Cov-2," New England Journal of Medicine, vol. 383, Issue 13, Sep. 24, 2020, 4 pages.

Xu, Hao, et al., "High expression of ACE2 receptor of 2019-nCoV on the epithelial cells of oral mucosa," International Journal of Oral Science, vol. 12, Issue 8, Feb. 24, 2020, 5 pages.

Soukos, Nikolaos, et al., "Phototargeting Oral Black-Pigmented Bacteria," Antimicrobial Agents and Chemotherapy, Apr. 2005, vol. 49, Issue 4, pp. 1391-1396.

Non-Final Office Action for U.S. Appl. No. 17/117,889, mailed Mar. 19, 2021, 17 pages.

Applicant-Initiated Interview Summary for U.S. Appl. No. 17/117,889, mailed Apr. 19, 2021, 2 pages.

Final Office Action for U.S. Appl. No. 17/117,889, mailed Apr. 30, 2021, 19 pages.

(56) References Cited

OTHER PUBLICATIONS

Author Unknown, "Scientific Breakthrough: Phototherapy Device," Facebook Timeline Photo, medicsBLU, Oct. 1, 2020, facebook.com/medicsblu/, 4 pages.
Ankhzaya, "Airway management," slideshow, www.slideshare.net/gasilu/airway-management-111268937, Aug. 24, 2018, 87 pages.
Liu, et al., "Creation of a standardized geometry of the human nasal cavity," Journal of Applied Physiology, vol. 106, Jan. 2009, pp. 784-795.
International Search Report and Written Opinion for International Patent Application No. PCT/US2021/019785, mailed Jun. 15, 2021, 18 pages.
Final Office Action for U.S. Appl. No. 16/709,550, mailed Feb. 17, 2021, 12 pages.
Advisory Action and Examiner-Initiated Interview Summary for U.S. Appl. No. 17/117,889, mailed May 19, 2021, 5 pages.
Advisory Action for U.S. Appl. No. 17/117,889, mailed Jun. 4, 2021, 3 pages.
Second Office Action for Chinese Patent Application No. 202010561507.X, mailed Jul. 15, 2022, 33 pages.
Advisory Action for U.S. Appl. No. 17/410,166, mailed Sep. 7, 2022, 3 pages.
Final Office Action for U.S. Appl. No. 17/201,120, mailed Sep. 23, 2022, 34 pages.
International Search Report and Written Opinion for International Patent Application No. PCT/US2022/019428, mailed Jun. 14, 2022, 16 pages.
Examination Report for European Patent Application No. 16831333.6, mailed May 20, 2022, 6 pages.
Advisory Action and Examiner-Initiated Interview Summary for U.S. Appl. No. 17/410,154, mailed Jul. 5, 2022, 4 pages.
Final Office Action for U.S. Appl. No. 17/410,166, mailed Jul. 1, 2022, 16 pages.
Non-Final Office Action for U.S. Appl. No. 17/162,259, mailed Jul. 6, 2022, 17 pages.
Non-Final Office Action for U.S. Appl. No. 17/410,154, mailed Jul. 28, 2022, 21 pages.
Technical Examination Report for Brazilian Patent Application No. 122020024964-1, mailed Nov. 29, 2022, 6 pages.
Advisory Action and Examiner-Initiated Interview Summary for U.S. Appl. No. 17/410,154, mailed Jan. 10, 2023, 4 pages.
Notice of Allowance for U.S. Appl. No. 17/410,166, mailed Feb. 15, 2023, 8 pages.
Advisory Action for U.S. Appl. No. 17/162,259, mailed Jan. 9, 2023, 3 pages.
Final Office Action for U.S. Appl. No. 17/173,457, mailed Feb. 23, 2023, 9 pages.
Notice of Allowance and Examiner-Initiated Interview Summary for U.S. Appl. No. 17/201,120, mailed Jan. 19, 2023, 21 pages.
Examination Report for Australian Patent Application No. 2021239894, mailed Nov. 9, 2021, 3 pages.
First Office Action for Chinese Patent Application No. 202010561507.X, mailed Oct. 19, 2021, 54 pages.
Non-Final Office Action for U.S. Appl. No. 17/410,154, mailed Nov. 8, 2021, 16 pages.
Final Office Action for U.S. Appl. No. 17/410,154, mailed Dec. 22, 2021, 15 pages.
Abeyakirthi, Sharnika, "Nitric oxide," DermNet NZ, 2009, 4 pages, www.dermnetnz.org/topics/nitric-oxide/.
Adamskaya, Natalia et al., "Light therapy by blue LED improves wound healing in an excision model in rats," Injury, 2010, 5 pages.
Adusumilli, Nagasai, et al., "Harnessing nitric oxide for preventing, limiting and treating the severe pulmonary consequences of COVID-19," Nitric Oxide, vol. 103, Jul. 2020, Elsevier Inc., 5 pages.
Akerstrom, Sara, et al., "Nitric Oxide Inhibits the Replication Cycle of Severe Acute Respiratory Syndrome Coronavirus," Journal of Virology, vol. 79, Issue 3, Feb. 2005, pp. 1966-1969.
Akerstrom, Sara, et al., "Dual effect of nitric oxide on SARS-CoV replication: Viral RNA production and palmitoylation of the S protein are affected," Virology, vol. 395, Oct. 2009, Elsevier Inc., 9 pages.
Andrew, Penelope J. et al., "Enzymatic function of nitric oxide synthases," Cardiovascular Research, vol. 43, No. 3, Aug. 15, 1999, pp. 521-531.
Author Unknown, "Brilliant Light Therapy," In Light Wellness Systems, eBrochure, Date Unknown, 5 pages.
Author Unkown, "dpl Oral Care—For Healthy Teeth & Gums," Product Brief, Revive Light Therapy, revivelighttherapy.com/product/dpl-oral-care-light-therapy-system-teeth-whitening/, accessed Jan. 31, 2021, 5 pages.
Author Unknown, "Healed by Light," Digi-Key Electronics, Jul. 1, 2014, 4 pages, www.digikey.com/es/articles/techzone/2014/jul/healed-by-light.
Author Unknown, "illuMask," La Lumière, Date Unknown, 2 pages, http://www.illumask.com/dimming/.
Author Unknown, "IPL Hair Removal," Spectrum Science & Beauty, Spectrum Blog, Sep. 16, 2014, 3 pages, www.spectrumsciencebeauty.com.au/ipl-hair-removal/#prettyPhoto.
Author Unknown, "Near-IR Photoluminescent Dyes for Molecular Labeling," NanoQuantum, Technology, 2013, 7 pages, www.nanoquantum.com/Technology.html.
Author Unknown, "Philips Blue Touch," Koninklijke Philips N.V., Version 1.0.1, Sep. 1, 2013, 2 pages.
Author Unknown, "Safety and Efficacy of UVC to Fight Covid-19," Gilbert W. Beebe Webinar Series, Program Agenda, Sep. 16, 2020, 6 pages.
Author Unknown, "Theradome Laser Helmet Review—A 120 Day Continuous Journal," Prevent Hair Loss Products, Jan. 14, 2014, retrieved Jun. 27, 2017, web.archive.org/web/20140610024017/http://preventhairlossproducts.com:80/theradome-laser-helmet-review-120-day-continuous-journal/, pp. 1-4.
Author Unknown, "Ultraviolet Light Therapy," Wound Care Centers, Date Unknown, 3 pages, www.woundcarecenters.org/article/wound-therapies/ultraviolet-light-therapy.
Author Unknown, "Vio Orb—Antimicrobial Light Ball," Product Brief, Revive Light Therapy, revivelighttherapy.com/product/envirohygiene-orb-antimicrobial-light-ball/, accessed Jan. 31, 2021, 6 pages.
Author Unknown, "What is Light Therapy used for?" Rio, The Dezac Group, Ltd, Date Unknown, 4 pages, www.lightmask.com/uses_for_lt.htm#top.
Avci, Pinar et al., "Low-Level Laser (Light) Therapy (LLLT) for Treatment of Hair Loss," Lasers in Surgery and Medicine, vol. 46, 2014, pp. 144-151.
Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.
Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.
Barolet, Daniel, "Light-Emitting Diodes (LEDs) in Dermatology," Seminars in Cutaneous Medicine and Surgery, vol. 27, No. 4, Dec. 1, 2008, pp. 227-238.
Bashkatov et al., "Optical properties of human skin, subcutaneous and mucous tissues in the wavelength range from 400-2000 nm," Journal of Physics D: Applied Physics, vol. 38, Jul. 2005, IOP Publishing Ltd, pp. 2543-2555.
Beck, Sara, et al., "Comparison of UV-Induced Inactivation and RNA Damage in MS2 Phage across the Germicidal UV Spectrum," Applied and Environmental Microbiology, vol. 82, Issue 5, Mar. 2016, pp. 1468-1474.
Beigel, JH, et al., "Remdesivir for the Treatment of Covid-19—Final Report," New England Journal of Medicine, vol. 383, Issue 19, Nov. 5, 2020, pp. 1813-1826.
Besaratinia, Ahmad, et al., "DNA lesions induced by UV A1 and B radiation in human cells: Comparative analyses in the overall genome and in the p53 tumor suppressor gene," PNAS, vol. 102, Issue 29, Jul. 2005, pp. 10058-10063.

(56) References Cited

OTHER PUBLICATIONS

Buonnano, Manuela, et al., "Far-UVC light (222 nm) efficiently and safely inactivates airborne human coronaviruses," Scientific Reports, Jun. 24, 2020, 8 pages.
Buonnano, Manuela, et al., "Germicidal Efficacy and Mammalian Skin Safety of 222-nm UV Light," Radiation Research, vol. 187, 2017, Radiation Research Society, 2017, pp. 493-501.
Cals-Grierson, M.-M. et al., "Nitric oxide function in the skin," Nitric Oxide, vol. 10, No. 4, Jun. 2004, pp. 179-193.
Chaves, Maria Emília de Abreu et al., "Effects of low-power light therapy on wound healing: Laser x LED," Anais Brasileiros de Dermatologia, vol. 89, No. 4, Jul./Aug. 2014, pp. 616-623.
Chen, Luni, et al., "Inhalation of Nitric Oxide in the Treatment of Severe Acute Respiratory Syndrome: A Rescue Trial in Beijing," Brief Report, Clinical Infectious Diseases, vol. 39, Oct. 2004, pp. 1531-1535.
Creagh-Brown, Benedict, et al., "Bench-to-bedside review: Inhaled nitric oxide therapy in adults," Critical Care, vol. 13, Issue 3, May 2009, BioMed Central Ltd, 8 pages.
Dai, Tianhong, et al., "Blue light for infectious diseases: Propionibacterium acnes, Helicobacter pylori, and beyond?," NIH-PA, Author Manuscript, 2012, Elsevier Ltd., 31 pages.
Darnelll, Miriam, et al., "Evaluation of inactivation methods for severe acute respiratory syndrome coronavirus in noncellular blood products," Transfusion, vol. 46, Oct. 2006, 8 pages.
De Marco, Federico, "Oxidative Stress and HPV Carcinogenesis," Viruses, vol. 5, Feb. 2013, pp. 708-731.
Donnarumma, G., et al., "Inhibition of HSV-1 Replication by Laser Diode-Irradiation: Possible Mechanism of Action," Journal of Immunopathology and Pharmacology, vol. 23, Issue 4, 2010, Biolife, pp. 1167-1176.
Dorrington, Michael, et al., "NF-KB Signaling in Macrophages: Dynamics, Crosstalk, and Signal Integration," Frontiers in Immunology, vol. 10, Apr. 9, 2019, 12 pages.
Eadie, Ewan, et al., "Extreme Exposure to Filtered Far-UVC: A Case Study," Ninewells Hospital and Medical School, Sep. 25, 2020, 14 pages.
Enwemeka, Chukuka, et al., "Blue 470-nm Light Kills Methicillin-Resistant *Staphylococcus aureus* (MRSA) in Vitro," Photomedicine and Laser Surgery, vol. 27, Issue 2, 2009, 6 pages.
Enwemeka, Chukuka, et al., "Light as a potential treatment for pandemic coronavirus infections: A perspective," Journal of Photochemistry & Photobiology, B: Biology, vol. 207, May 2020, 7 pages.
Enwemeka, Chukuka, et al., "Visible 405 nm SLD Light Photo-Destroys Methicillin-Resistant *Staphylococcus aureus* (MRSA) In Vitro," Lasers in Surgery and Medicine, vol. 40, 2008, pp. 734-737.
Farivar, Shirin et al., "Biological Effects of Low Level Laser Therapy," Journal of Lasers in Medical Sciences, vol. 5, No. 2, Spring 2014, pp. 58-62.
Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.
Ferrari-Light, Dana, et al., "The Utility of Near-Infrared Fluorescence and Indocyanine Green During Robotic Pulmonary Resection," Frontiers in Surgery, Review, vol. 6, Aug. 2019, 7 pages.
Finsen, Niels, "The Red Light Treatment of Small-Pox," The British Medical Journal, Dec. 7, 1895, pp. 1412-1414.
Garza, Felix, et al., "Visible Blue Light Therapy: Molecular Mechanisms and Therapeutic Opportunities," Current Medical Chemistry, 2018, vol. 25, Bentham Science Publishers, pp. 5564-5577.
Glazer-Hockstein, "Could Blue Light-Blocking Lenses Decrease the Risk of Age-Related Macular Degeneration," Retina, vol. 26, 2006, 4 pages.
Gupta, Asheesh et al., "History and Fundamentals of Low-Level Laser (Light) Therapy," Handbook of Photomedicine, Chapter 5, CRC Press, 2014, pp. 43-52.
Hamblin, Michael, et al., "Can light-based approaches overcome antimicrobial resistance?," Drug Development Research, Jul. 2018, Wiley Periodicals, Inc., 20 pages.
Hamblin, Michael, et al., "Mechanisms of Low Level Light Therapy," Proceedings of the SPIE, vol. 6140, Feb. 10, 2006, pp. 614001-1 to 641001-12.
Arora, Prerna, et al., "B.1.617.2 enters and fuses lung cells with increased efficiency and evades antibodies induced by infection and vaccination," Cell Reports, vol. 37, Oct. 12, 2021, 12 pages.
Caly, Leon, et al., "The FDA-approved drug ivermectin inhibits the replication of SARS-CoV-2 in vitro," Antiviral Research, vol. 178, Apr. 3, 2020, Elsevier B.V., 4 pages.
Cele, Sandile, et al., "Escape of SARS-CoV-2 501Y.V2 from neutralization by convalescent plasma," Nature, vol. 593, May 6, 2021, 18 pages.
Cheng, Ya-Wen, et al., "D614G Substitution of SARS-CoV-2 Spike Protein Increases Syncytium Formation and Virus Titer via Enhanced Furin-Mediated Spike Cleavage," mBio, vol. 12, Issue 4, Jul. 27, 2021, 11 pages.
Do, et al., "A robust SARS-CoV-2 replication model in primary human epithelial cells at the air liquid interface to assess antiviral agents," Antiviral Research, vol. 192, Jun. 26, 2021, Elsevier, B.V., 8 pages.
Fulcher, et al., "Human Nasal and Tracheo-Bronchial Respiratory Epithelial Cell Culture," Methods in Molecular Biology, vol. 945, Chapter 8, 2012, pp. 109-121.
Gong, et al., "Contribution of single mutations to selected SARS-CoV-2 emerging variants spike antigenicity," Virology, vol. 563, Sep. 11, 2021, Elsevier Inc., 12 pages.
Good, Steven, et al., "AT-527 a Double Prodrug of a Guanosine Nucleotide Analog, Is a Potent Inhibitor of SARS-CoV-2 In Vitro and a Promising Oral Antiviral for Treatment of Covid-19," Antimicrobial Agents and Chemotherapy, vol. 65, Issue 4, Apr. 2021, 12 pages.
Harvey, William, et al., "SARS-CoV-2 variants, spike mutations and immune escape," Nature Reviews: Microbiology, vol. 19, Jul. 2021, pp. 409-424.
Heinen, Natalie, et al., "In Vitro Lung Models and Their Application to Study SARS-CoV-2 Pathogenesis and Disease," Viruses, vol. 13, Apr. 28, 2021, 17 pages.
Hou, Yixuan, et al., "SARS-CoV-2 Reverse Genetics Reveals a Variable Infection Gradient in the Respiratory Tract," Cell, vol. 182, Jul. 23, 2020, Elsevier Inc., 32 pages.
Huang, Ni, et al., "SARS-CoV-2 infection of the oral cavity and saliva," Nature Medicine, vol. 27, May 2021, 27 pages.
Krause, Philip, et al., "SARS-CoV-2 Variants and Vaccines," New England Journal of Medicine, vol. 385, Issue 2, Jul. 8, 2021, Massachusetts Medical Society, pp. 179-186.
Kumar, Sanjeev, et al., "Current status of therapeutic monoclonal antibodies against SARS-CoV-2," PLOS Pathogens, Sep. 3, 2021, 8 pages.
Levin, "Waning Immune Humoral Response to BNT162b2 Covid-19 Vaccine over 6 Months," New England Journal of Medicine, Oct. 6, 2021, Massachusetts Medical Society, 11 pages.
Liu, Haolin, et al., "The Lambda variant of SARS-CoV-2 has a better chance than the Delta variant to escape vaccines," Aug. 26, 2021, bioRxiv, 26 pages.
Liu, Jia, et al., "Hydroxychloroquine, a less toxic derivative of chloroquine, is effective in inhibiting SARS-CoV-2 infection in vitro," Cell Discovery, vol. 6, Issue 16, Mar. 18, 2020, 4 pages.
Liu, Yang, "Delta spike P681R mutation enhances SARS-CoV-2 fitness over Alpha variant," Sep. 5, 2021, bioRxiv, 29 pages.
Marchesan, et al., "The 'oral' history of COVID-19: Primary infection, salivary transmission, and post-acute implications," Journal of Periodontology, vol. 92, American Academy of Periodontology, Jul. 2021, pp. 1357-1367.
Mccullough, Peter, et al., "Pathophysiological Basis and Rationale for Early Outpatient Treatment of SARS-CoV-2 (COVID-19) Infection," The American Journal of Medicine, Review, vol. 134, Issue 1, Jan. 2021, Elsevier Inc., pp. 16-22.
Motozono, Chihiro, et al., "SARS-CoV-2 spike L452R variant evades cellular immunity and increases infectivity," Cell Host and Microbe, vol. 29, Jul. 14, 2021, Elsevier Inc., 24 pages.

(56) References Cited

OTHER PUBLICATIONS

Naaber, Paul, et al., "Dynamics of antibody response to BNT162b2 vaccine after six months: a longitudinal prospective study," The Lancet Regional Health—Europe, Sep. 6, 2021, 9 pages.
Planas, Delphine, et al., "Reduced sensitivity of SARS-CoV-2 variant Delta to antibody neutralization," Nature, vol. 596, Jul. 8, 2021, 20 pages.
Plante, Jessica, et al., "Spike mutation D614G alters SARS-CoV-2 fitness," Nature, vol. 592, Oct. 26, 2020, 22 pages.
Pouwels, Koen, et al., "Effect of Delta variant on viral burden and vaccine effectiveness against new SARS-CoV-2 infections in the UK," Nature Medicine, Oct. 14, 2021, 25 pages.
Pruijssers, Andrea, et al., "Remdesivir Inhibits SARS-CoV-2 in Human Lung Cells and Chimeric SARS-CoV Expressing the SARS-CoV-2 RNA Polymerase in Mice," Cell Reports, vol. 32, Jul. 21, 2020, 15 pages.
Sellgren, et al., "A biomimetic multicellular model of the airways using primary human cells," Lab on a Chip, Jun. 2014, The Royal Society of Chemistry, 10 pages.
Sheahan, Timothy, et al., "An orally bioavailable broad-spectrum antiviral inhibits SARS-CoV-2 in human airway epithelial cell cultures and multiple coronaviruses in mice," Science Translational Medicine, Research Article, vol. 12, Apr. 29, 2020, 16 pages.
Stasko, Nathan, et al., "A randomized, controlled, feasibility study of RD-X19 in patients with mild-to-moderate COVID-19 in the outpatient setting," Oct. 25, 2021, medRxiv, 30 pages.
Stasko, Nathan, et al., "Visible blue light inhibits infection and replication of SARS-CoV-2 at doses that are well-tolerated by human respiratory tissue," Scientific Reports, vol. 11, Oct. 18, 2021, 14 pages.
Touret, Franck, et al., "Preclinical evaluation of Imatinib does not support its use as an antiviral drug against SARS-CoV-2," Antiviral Research, vol. 193, Jul. 12, 2021, 8 pages.
Touret, Franck, et al., "Replicative Fitness of a SARS-CoV-2 201/501Y.V1 Variant from Lineage B.1.1.7 in Human Reconstituted Bronchial Epithelium," mBio, vol. 12, Issue 4, Jul. 2021, 4 pages.
Wang, Pengfei, et al., "Antibody resistance of SARS-CoV-2 variants B.1.351 and B.1.1.7," Nature, vol. 593, May 6, 2021, 18 pages.
Wildera, Marek, et al., "Limited Neutralization of Authentic Severe Acute Respiratory Syndrome Coronavirus 2 Variants Carrying E484K In Vitro," The Journal of Infectious Diseases, Jul. 5, 2021, pp. 1109-1114.
Final Office Action for U.S. Appl. No. 16/709,550, mailed Dec. 27, 2021, 9 pages.
Advisory Action for U.S. Appl. No. 17/410,154, mailed Jan. 25, 2022, 3 pages.
Non-Final Office Action for U.S. Appl. No. 17/410,166, mailed Jan. 12, 2022, 12 pages.
Notice of Allowance for U.S. Appl. No. 16/709,550, mailed Feb. 24, 2022, 8 pages.
Corrected Notice of Allowability for U.S. Appl. No. 16/709,550, mailed Mar. 25, 2022, 5 pages.
Corrected Notice of Allowability for U.S. Appl. No. 16/709,550, mailed Apr. 15, 2022, 5 pages.
Final Office Action for U.S. Appl. No. 16/898,385, mailed Feb. 15, 2022, 13 pages.
Advisory Action for U.S. Appl. No. 16/898,385, mailed Apr. 20, 2022, 4 pages.
Non-Final Office Action for U.S. Appl. No. 17/410,154, mailed Feb. 24, 2022, 21 pages.
Final Office Action for U.S. Appl. No. 17/410,154, mailed May 13, 2022, 18 pages.
Final Office Action for U.S. Appl. No. 17/410,166, mailed Mar. 14, 2022, 13 pages.
Advisory Action for U.S. Appl. No. 17/410,166, mailed May 11, 2022, 3 pages.
Non-Final Office Action for U.S. Appl. No. 17/201,120, mailed Apr. 15, 2022, 23 pages.
Notification of Reasons for Rejection for Japanese Patent Application No. 2021-518715, mailed Apr. 26, 2022, 9 pages.
Non-Final Office Action for U.S. Appl. No. 16/898,385, mailed Jun. 7, 2022, 13 pages.
Non-Final Office Action for U.S. Appl. No. 17/410,166, mailed May 27, 2022, 11 pages.
Notice of Acceptance for Australian Patent Application No. 2021239894, mailed Jun. 15, 2022, 3 pages.
Non-Final Office Action for U.S. Appl. No. 16/709,550, mailed Jul. 12, 2021, 12 pages.
Non-Final Office Action for U.S. Appl. No. 16/898,385, mailed Aug. 16, 2021, 12 pages.
Notice of Allowance for U.S. Appl. No. 17/117,889, mailed Aug. 30, 2021, 9 pages.
Final Office Action for U.S. Appl. No. 17/148,124, mailed Mar. 13, 2023, 29 pages.
Notice of Allowance and Examiner-Initiated Interview Summary for U.S. Appl. No. 17/410,154, mailed Mar. 9, 2023, 14 pages.
Non-Final Office Action for U.S. Appl. No. 17/162,259, mailed Apr. 7, 2023, 18 pages.
Final Office Action for U.S. Appl. No. 17/162,283, mailed Apr. 10, 2023, 10 pages.
Advisory Action for U.S. Appl. No. 17/173,457, mailed May 1, 2023, 3 pages.
International Search Report and Written Opinion for International Patent Application No. PCT/US2023/015757, mailed Jun. 30, 2023, 14 pages.
Non-Final Office Action for U.S. Appl. No. 17/148,108, mailed Jul. 19, 2023, 14 pages.
Advisory Action and Examiner-Initiated Interview Summary for U.S. Appl. No. 17/148,124, mailed May 26, 2023, 5 pages.
Non-Final Office Action for U.S. Appl. No. 17/148,133, mailed Jun. 15, 2023, 9 pages.
Final Office Action for U.S. Appl. No. 17/162,259, mailed Jul. 14, 2023, 18 pages.
Advisory Action for U.S. Appl. No. 17/162,283, mailed Jun. 23, 2023, 3 pages.
Non-Final Office Action for U.S. Appl. No. 17/173,457, mailed Jun. 9, 2023, 9 pages.
Non-Final Office Action for U.S. Appl. No. 17/162,259, mailed Sep. 1, 2023, 11 pages.
Non-Final Office Action for U.S. Appl. No. 17/117,858, mailed Oct. 13, 2023, 16 pages.
Final Office Action for U.S. Appl. No. 17/148,108, mailed Oct. 27, 2023, 15 pages.
Final Office Action for U.S. Appl. No. 17/148,133, mailed Oct. 4, 2023, 10 pages.
Advisory Action for U.S. Appl. No. 17/162,259, mailed Sep. 21, 2023, 3 pages.
Non-Final Office Action for U.S. Appl. No. 17/162,259, mailed Oct. 26, 2023, 18 pages.
Non-Final Office Action for U.S. Appl. No. 17/162,283, mailed Sep. 1, 2023, 11 pages.
Notice of Allowance and Examiner-Initiated Interview Summary for U.S. Appl. No. 17/173,457, mailed Oct. 17, 2023, 10 pages.
Office Action for Canadian Patent Application No. 3174573, mailed Oct. 20, 2023, 4 pages.
Notice of Allowance for Brazilian Patent Application No. BR1122020024964-1, mailed Nov. 27, 2023, 4 pages.
Non-Final Office Action for U.S. Appl. No. 17/148,090, mailed Dec. 13, 2023, 12 pages.
Non-Final Office Action for U.S. Appl. No. 17/148,124, mailed Dec. 18, 2023, 24 pages.
Advisory Action for U.S. Appl. No. 17/148,133, mailed Dec. 8, 2023, 3 pages.
Author Unknown, "Visible spectrum," Wikipedia article, en.wikipedia.org/wiki/Visible_spectrum, accessed 2024, 11 pages.
Written Decision on Registration for Korean Patent Application No. 10-2022-7036254, mailed Mar. 20, 2024, 8 pages.
Advisory Action for U.S. Appl. No. 17/117,858, mailed Apr. 26, 2024, 3 pages.
Final Office Action for U.S. Appl. No. 17/148,090, mailed May 6, 2024, 9 pages.
Final Office Action for U.S. Appl. No. 17/117,858, mailed Feb. 14, 2024, 11 pages.

(56) References Cited

OTHER PUBLICATIONS

Advisory Action for U.S. Appl. No. 17/148,108, mailed Jan. 3, 2024, 3 pages.
Applicant-Initiated Interview Summary for U.S. Appl. No. 17/148,108, mailed Jan. 23, 2024, 2 pages.
Non-Final Office Action for U.S. Appl. No. 17/148,108, mailed Feb. 20, 2024, 10 pages.
Notice of Allowance for U.S. Appl. No. 17/148,133, mailed Jan. 24, 2024, 8 pages.
Notice of Allowance for U.S. Appl. No. 17/162,283, mailed Feb. 12, 2024, 8 pages.
Notice of Allowance for U.S. Appl. No. 17/173,457, mailed Jan. 29, 2024, 10 pages.
Examination Report for European Patent Application No. 16831333.6, mailed May 7, 2024, 7 pages.
International Search Report and Written Opinion for International Patent Application No. PCT/US2024/016811, mailed May 29, 2024, 14 pages.
Notice of Allowance for U.S. Appl. No. 17/117,858, mailed May 22, 2024, 7 pages.
Final Office Action for U.S. Appl. No. 17/148,124, mailed May 28, 2024, 23 pages.
Final Office Action for U.S. Appl. No. 17/162,259, mailed May 20, 2024, 22 pages.
Office Action for Canadian Patent Application No. 3174573, mailed Aug. 5, 2024, 4 pages.
Examination Report for European Patent Application No. 21713288.5, mailed Aug. 19, 2024, 4 pages.
Advisory Action for U.S. Appl. No. 17/148,090, mailed Jul. 9, 2024, 3 pages.
Notice of Allowance for U.S. Appl. No. 17/148,108, mailed Jul. 10, 2024, 8 pages.
Advisory Action and Examiner-Initiated Interview Summary for U.S. Appl. No. 17/148,124, mailed Aug. 9, 2024, 6 pages.
Advisory Action for U.S. Appl. No. 17/162,259, mailed Jul. 25, 2024, 3 pages.

\* cited by examiner

DEVICES AND METHODS FOR ILLUMINATING TISSUE TO INDUCE BIOLOGICAL EFFECTS

FIELD OF THE DISCLOSURE

The present disclosure is related to devices and methods for illuminating tissue to induce one or more biological effects.

BACKGROUND

Phototherapy, which is the exposure of the body to one or more types of light to induce a biological effect, is currently being studied for various health related medical benefits. Studies have shown that phototherapy may be beneficial for promotion of hair growth, treatment of skin or tissue inflammation, promoting tissue or skin healing or rejuvenation, enhancing wound healing, pain management, reduction of wrinkles, scars, stretch marks, varicose veins, and spider veins, treating cardiovascular disease, treating erectile dysfunction, treating microbial infections, treating hyperbilirubinemia, and treating various oncological and non-oncological diseases and disorders. Various mechanisms by which phototherapy has been suggested to provide therapeutic benefits include increasing circulation (e.g., by increasing the formation of new capillaries), stimulating the production of collagen, stimulating the release of adenosine triphosphate (ATP), enhancing porphyrin production, reducing excitability of nervous system tissues, modulating fibroblast activity, increasing phagocytosis, inducing thermal effects, stimulating tissue granulation and connective tissue phagocytosis, reducing inflammation, and stimulating acetylcholine release. Phototherapy has also been suggested to stimulate cells to produce nitric oxide, which may act as a signaling messenger, cytotoxin, antiapoptotic agent, antioxidant, and regulator of microcirculation. Nitric oxide is recognized to relax vasculature smooth muscles, dilate blood vessels, inhibit aggregation of platelets, and modulate T-cell mediated immune response. Generally, phototherapy shows promise for improving health and/or treating myriad medical conditions.

It is often desirable to concentrate the exposure of light to a specific portion of the body to achieve a therapeutic effect. In some situations, the efficacy of phototherapy will depend on the type of light and the dose of light (e.g., intensity over time) the portion of the body is exposed to. In some scenarios, it may be challenging to deliver a desired dose of light to a specific portion of the body. This may occur, for example, if the desired portion of the body is not immediately exposed, such as when the desired portion of the body is located within a body cavity. Accordingly, there is a need for improved devices and methods for administering phototherapy, and in particular to devices and methods for administering phototherapy to portions of the body that may be difficult to reach.

SUMMARY

In one embodiment, an illumination device includes a light source and a deformable light guide optically coupled to the light source. The deformable light guide is configured to conform to a surface of tissue when in contact with the tissue such that light from the light source is coupled directly from the deformable light guide to the tissue. By using a deformable light guide, more light can be delivered to a target tissue. This may increase treatment efficacy, reduce treatment time, or both.

In one embodiment, an illumination device includes a light source and a light guide optically coupled to the light source. The light source and the light guide are configured to irradiate light into an ancillary body cavity of a user via a primary body cavity of the user. In some situations, the ancillary body cavity may be difficult or uncomfortable to access for the irradiation of light for therapeutic purposes. By providing the light via the primary body cavity, these issues can be mitigated. In one embodiment, the primary body cavity is the oral cavity and the secondary body cavity is the nasal cavity.

In one embodiment, an illumination device includes a first light source, a second light source, and a light guide optically coupled to the first light source and the second light source. The light guide and the first light source are configured to irradiate light having one or more first light output characteristics on a first tissue area of a user. The light guide and the second light source are configured to irradiate light having one or more second light output characteristics onto a second tissue area of the user. The first tissue area is different from the second tissue area, and may be non-overlapping with the first tissue area. The one or more first light output characteristics are different from the one or more second light output characteristics, and may include one or more of peak wavelength, intensity, polarization, and duration of exposure. By providing different types of light (i.e., light having different light output characteristics) to different tissue areas of a user, different and sometimes synergistic therapeutic effects may be achieved.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

DETAILED DESCRIPTION

Figure 1:
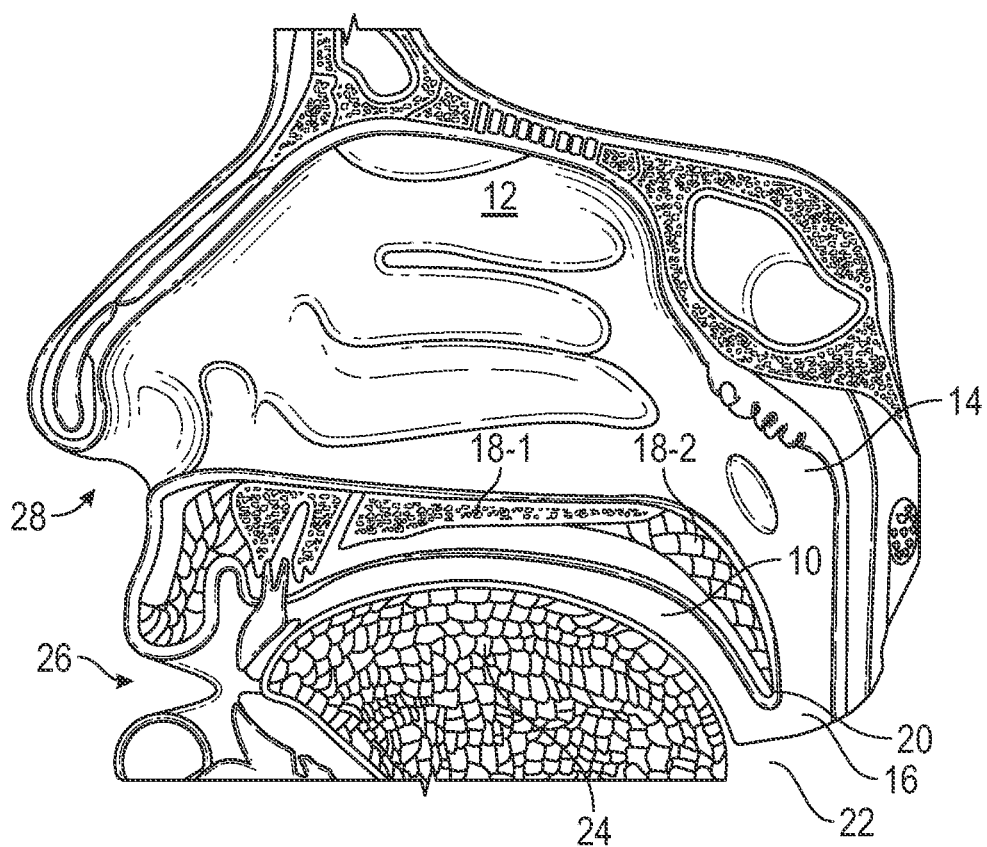
FIG. 1 is a cross-sectional view of an oral cavity and a nasal cavity.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

The present disclosure relates generally to devices and methods for impinging light on tissue to induce one or more biological effects, and more particularly to illumination devices and related methods that may be used for delivery of irradiation. Exemplary illumination devices may include a light guide that is optically coupled with a light source, where the light guide is deformable such that it conforms to tissue when in contact with the tissue and thus better couples light into the tissue. In additional embodiments, an illumination device may irradiate light into a body cavity. Further, the illumination device may irradiate light into an ancillary body cavity via a primary body cavity. In additional embodiments, an illumination device may include a first light source, a second light source, and a light guide optically coupled to the first light source and the second light source. The first light source and the light guide may be configured to irradiate light with one or more light output characteristics onto a first tissue area of a user, while the second light source and the light guide may be configured to irradiate light with one or more characteristics onto a second tissue area. The characteristics of the light irradiated onto the first tissue area and the light irradiated onto the second tissue area are different, such that they have a different peak wavelength, intensity (e.g., radiant flux), polarization, duration of exposure, etc. The first tissue area may be located in a different body cavity than the second tissue area.

Aspects of the present disclosure relate to devices and methods for impinging light on a mammalian tissue, for example within a body and/or a body cavity of a patient, where the light may include at least one characteristic that exerts or induces at least one biological effect within or on the tissue. Exemplary tissues include those of the upper respiratory tract, including tissues and cavities that are accessible via the oral cavity. Biological effects may include at least one of inactivating and inhibiting growth of one or more combinations of microorganisms and pathogens, including but not limited to viruses, bacteria, fungi, and other microbes, among others. Biological effects may also include one or more of upregulating and/or downregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissues and the targeted microorganisms and/or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Aspects of the present disclosure relate to devices and methods for treating, preventing, and/or reducing the biological activity of pathogens while they are in one or more areas of the upper respiratory tract and hopefully before they travel to the lungs or elsewhere in the body. In certain aspects, devices and methods as disclosed herein may prevent or reduce infections by reducing microbial load along intranasal passageways, decreasing the ability for penetration into cells at the site of infection, and amplifying host defense systems, all of which may minimize or avoid the need for traditional antimicrobial medicines.

The present disclosure is generally directed to illumination devices, apparatus, and methods for impinging light onto living tissue in order to induce one or more therapeutic biological effects. In various aspects, induced biological effects may include at least one of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain aspects, the light may be referred to as nitric-oxide modulating light to increase concentrations of unbound nitric oxide within living tissue. Embodiments of the present disclosure may administer light at one or more wavelengths as a pre-exposure prophylaxis or a post-exposure prophylaxis in order to eliminate pathogens in or on tissue of the upper respiratory tract and/or amplify host defense systems. Embodiments of the present disclosure may be used to prevent and/or treat respiratory infections and other infectious diseases. For example, in certain embodiments, a hand-held illumination device may administer light at one or more wavelengths as a prophylactic measure to counteract invading viral pathogens and corresponding diseases that may originate in the respiratory tract. In a specific example, light may be administered that reduces viral infectivity and incidence of COVID-19 in individuals who have been infected or believe they may have been exposed to SARS-CoV-2 virus. In certain aspects, illumination devices of the present disclosure may be provided or referred to as phototherapeutic and/or illumination devices.

The term "phototherapy" relates to the therapeutic use of light. As used herein, phototherapy may be used to treat and/or prevent microbial infections, including viral infections of the upper respiratory tract. The mechanisms by which certain wavelengths of light are effective can vary, depending on the wavelength that is administered and the targeted microorganisms and/or pathogens. Biological effects, including antimicrobial effects, can be provided over a wide range of wavelengths, including ultraviolet (UV) ranges, visible light ranges, and infrared ranges, and combinations thereof.

Various wavelengths of light may be irradiated on human tissue with little or no impact on tissue viability. As defined herein, light means visual and non-visual electromagnetic radiation with a peak wavelength between 200 nm and 4000 nm. In certain embodiments, various wavelengths of visible light may elicit antimicrobial and/or anti-pathogenic behavior in tissue of the respiratory tract, including any of the aforementioned biological effects. For example, light with a peak wavelength in a range from 410 nanometers (nm) to 450 nm may inactivate microorganisms that are in a cell-free environment and/or inhibit replication of microorganisms that are in a cell-associated environment and/or stimulate enzymatic generation of nitric oxide, while also upregulating a local immune response in target tissue. In this regard, light with a peak wavelength in a range from 400 nm to 450 nm may be well suited for fighting invading viral pathogens and corresponding diseases that may originate in the respiratory tract, including Orthomyxoviridae (e.g., influenza), common colds, coronaviridae (e.g., coronavirus), picornavirus infections, tuberculosis, pneumonia, bronchitis, and sinusitis. In certain embodiments, red light or near-infrared (NIR) light (e.g., peak wavelength range from 630 nm to 1,000 nm) may be useful to provide anti-inflammatory effects and/or to promote vasodilation. Anti-inflammatory effects may be useful in treating disorders, particularly microbial disorders that result in inflammation along the respiratory tract. In this regard, red light may be used as part of treatment protocols that reduce any tissue inflammation that may result from exposure to blue light, which may positively impact cell viability, thereby lowering cytotoxicity even further. A decrease in inflammation can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Depending on the application, other wavelength ranges of light may also be administered to human tissue. For example, UV light (e.g., UV-A light having a peak wavelength in a range of from 315 nm to 400 nm, UV-B light having a peak wavelength in a range of from 280 nm to 315 nm, and UV-C light having a peak wavelength in a range from 200 nm to 280 nm) may be effective for inactivating microorganisms that are in a cell-free environment and/or inhibit replication of microorganisms that are in a cell-associated environment and/or stimulate enzymatic generation of nitric oxide. However, overexposure to UV light may lead to cytotoxicity concerns in associated tissue. It may therefore be desirable to use shorter cycles and/or lower doses of UV light than corresponding treatments with only visible light. In certain embodiments, light with a peak wavelength in a range from 385 nm to 450 nm may be provided to elicit an antimicrobial and/or anti-pathogenic effect. In further embodiments, such wavelengths of light may be used in treatment protocols that also administer anti-inflammatory light.

An illumination device for the treatment of pathogens and/or for inducing one or more biological effects may take any form suitable for delivering light to the target tissue. The device may contain a light source capable of emitting a suitable light profile that can provide one or more direct or indirect biological effects. A light profile can be represented with a graph of emission intensity versus wavelength of light for any particular light source. In certain aspects, light sources may be provided with light output characteristics in the visible spectrum, for example with light emissions with peak wavelengths primarily in a range from 400 nm to 700 nm. Depending on the target application, light output characteristics may also include infrared or near-infrared peak wavelengths at or above 700 nm, or UV peak wavelengths at or below 400 nm. In certain embodiments, light emissions may have a single peak wavelength in a range from 200 nm to 1,000 nm, or in a range from 400 nm to 490 nm, or in a range from 400 nm to 435 nm, or in a range from 400 nm to 420 nm, or in a range from 400 nm to 440 nm, or in a range from 400 nm to 450 nm, or in a range from 420 nm to 440 nm, or in a range from 450 nm to 490 nm, or in a range from 500 nm to 900 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in from 630 nm to 670 nm, or in a range from 320 nm to 400 nm, or in a range from 385 nm to 450 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects. Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color light-emitting diodes (LEDs) in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad-spectrum LED may provide certain wavelengths that induce one or more biological effects while also providing broad spectrum emissions to the target area for illumination. In this regard, light impingement on tissue for single and/or multiple microorganisms and/or multiple pathogenic biological effects may be provided with light of a single peak wavelength or a combination of light with more than one peak wavelength.

In addition to providing light with a first peak wavelength, light sources discussed herein may also provide light at a second peak wavelength. The first peak wavelength may be in any of the ranges described herein, while the second peak wavelength may also be in any of the ranges described herein such that it is overlapping or non-overlapping with the first peak wavelength. In one embodiment, the first peak wavelength is in a range of 385 nm to 450 nm and the second peak wavelength is in a range from 620 nm to 1,000 nm.

Doses of light to induce one or more biological effects may be administered with one or more light output characteristics, including peak wavelengths, radiant flux, and irradiance to target tissues. Irradiances to target tissues may be provided in a range from 0.1 milliwatts per square centimeter ($mW/cm^2$) to 200 $mW/cm^2$, or in a range from 5 $mW/cm^2$ to 200 $mW/cm^2$, or in a range from 5 $mW/cm^2$ to 100 $mW/cm^2$, or in a range from 5 $mW/cm^2$ to 60 $mW/cm^2$, or in a range from 60 $mW/cm^2$ to 100 $mW/cm^2$, or in a range from 100 $mW/cm^2$ to 200 $mW/cm^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in another range specified herein. Depending on the configuration of one or more of the light sources, the corresponding illumination device, and the distance away from a target tissue, the radiant flux value for the light source may be higher than the irradiance value at the tissue.

While certain peak wavelengths for certain target tissue types may be administered with irradiances up to 1 $W/cm^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 $W/cm^2$ to 10 $W/cm^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered over a number of times to provide a cumulative or total dose over a cumulative time period. By way of example, a single dose of light as disclosed herein may be provided over a single time period, such as in a range from 100 nanoseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter ($J/cm^2$) to 100 $J/cm^2$, or in a range from 0.5 $J/cm^2$ to 50 $J/cm^2$, or in a range from 2 $J/cm^2$ to 80 $J/cm^2$, or in a range from 5 $J/cm^2$ to 50 $J/cm^2$, while corresponding cumulative doses may be provided in a range from 1 $J/cm^2$ to 1000 $J/cm^2$, or in a range from 1 $J/cm^2$ to 500 $J/cm^2$, or in a range from 1 $J/cm^2$ to 200 $J/cm^2$, or in a range from 1 $J/cm^2$ to 100 $J/cm^2$, or in a range from 4 $J/cm^2$ to 160 $J/cm^2$, or in a range from 10 $J/cm^2$ to 100 $J/cm^2$, among other disclosed ranges. In a specific example, a single dose may be administered in a range from 10 $J/cm^2$ to 20 $J/cm^2$, and the single dose may be repeated twice a day for four consecutive days to provide a cumulative dose in a range from 80 $J/cm^2$ to 160 $J/cm^2$. In another specific example, a single dose may be administered at about 30 $J/cm^2$, and the single dose may be repeated twice a day for seven consecutive days to provide a cumulative dose of 420 $J/cm^2$.

In still further aspects, light for inducing one or more biological effects may include administering different doses of light to a target tissue to induce one or more biological effects for different target pathogens. As disclosed herein, a biological effect may include altering a concentration of one or more pathogens within the body and altering growth of the one or more pathogens within the body. The biological effect may include at least one of inactivating a first pathogen in a cell-free environment, inhibiting replication of the first pathogen in a cell-associated environment, upregulating a local immune response in mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. As further disclosed herein, a pathogen may include a virus, a bacteria, and a fungus, or any other types of microorganisms that can cause infections. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at a time, one to a few times a day, and the beneficial effect of the phototherapy may continue in between treatments.

Light sources may include one or more of LEDs, organic LEDs (OLEDs), lasers and other lamps according to aspects of the present disclosure. Lasers may be used for irradiation in combination with optical fibers or other delivery mechanisms. LEDs are solid state electronic devices capable of emitting light when electrically activated. LEDs may be configured across many different targeted emission spectrum bands with high efficiency and relatively low costs. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to provide irradiances as high as 100 $mW/cm^2$, or 200 $mW/cm^2$ in the desired wavelength range. An LED array in this device can be incorporated into an irradiation head, hand piece and/or as an external unit.

According to aspects of the present disclosure, exemplary target tissues and cells for light treatments may include one or more tissues of the upper respiratory tract, including the nasal cavity, ostium from paranasal sinus cavities, and the pharynx, including the nasopharynx and the oropharynx. FIG. 1 is an illustration representing a cross-sectional view of an oral cavity 10 and a nasal cavity 12. The nasal cavity 12 includes the nasopharynx 14 and the oropharynx 16. As will be further described below in greater detail, aspects of the present disclosure are related to devices and methods for providing therapeutic doses of light within the oral cavity 10, the nasal cavity 12 and/or other parts of the body, including the nasopharynx 14 and oropharynx 16, by way of the oral cavity 10. The oral cavity 10 is located below the nasal cavity 12. The oral cavity 10 is separated from the nasal cavity 10 via the palate 18, which includes the hard palate 18-1 which is formed primarily of bone and the soft palate 18-2 which is formed primarily of tissue. The uvula 20 is located at the back of the oral cavity 10 and hangs down into the throat 22. The tongue 24 rests at the bottom of the oral cavity 10. The oral cavity 10 can be accessed via the mouth 26. The nasal cavity 12 can be accessed via one or more of the nostrils 28.

As discussed above, research has shown promise for the benefits of light irradiation onto one or more portions of the oral cavity 10 and/or the nasal cavity 12. With regard to the nasal cavity 12, irradiation of light into the nasal cavity 12 has generally required inserting a device into one or more of the nostrils 28. This can often be uncomfortable for a user, especially when a desired dose of light requires extended time to be delivered. This is especially true when considering irradiation of the nasopharynx 16 with light. Since the nasopharynx 14 is located deep within the nasal cavity 12, irradiating it with light has thus far required inserting a device deep into one or more of the nostrils 28, which, as stated above can be highly uncomfortable for the user.

Figure 2:
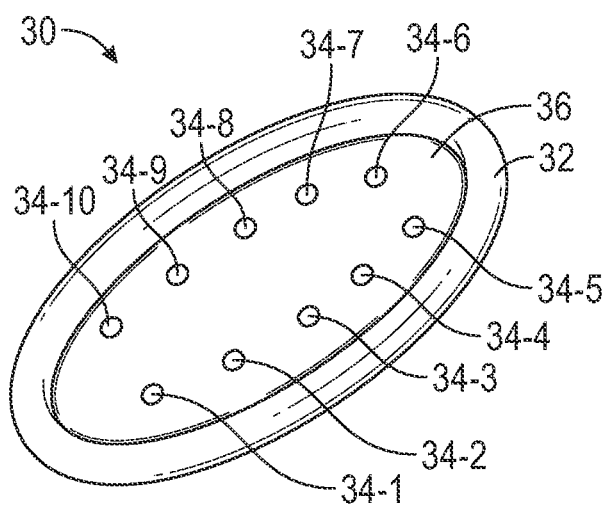
FIG. 2 is an isometric view of an illumination device according to one embodiment of the present disclosure.

FIG. 2 shows an isometric view of an illumination device 30 according to one embodiment of the present disclosure. The illumination device 30 includes a housing 32, a number of light sources 34 (shown individually as 34-1 through 34-10), and a deformable light guide 36. The light source 34 and the deformable light guide 36 are integrated into the housing 32. The light source 34 is configured to provide light having one or more desired light output characteristics. The deformable light guide 36 is optically coupled to the light source 34 and configured to guide the light produced by the light source 34 to a specified location (e.g., a target tissue area) via a primary emission surface, which in the present embodiment is the surface of the deformable light guide 36. Notably, the deformable light guide 36 is configured to conform to a target tissue of a user when in contact with the tissue. This may allow for better delivery of light to the target tissue due to direct coupling of the light to the target tissue and thus less light losses (e.g., due to refraction and reflection) by direct coupling of the light into the target tissue. As discussed herein, "direct coupling" of light into tissue means providing light from the deformable light guide 32 into the tissue such that the light does not need to travel through air before reaching the target tissue.

The illumination device 30 may be configured to be provided partially or completely within the oral cavity 10 of the user. In such an embodiment, the deformable light guide 36 may be configured to conform to the roof of the mouth of the user against the palate 18 such that the primary emission surface is along the roof of the mouth directed at the palate 18. Accordingly, the deformable light guide 36 may be provided with a convex shape suitable for conforming to the roof of the mouth, and further the material of the deformable light guide 36 may be soft enough to conform to the individual curves within the roof of the mouth of the user. However, in other embodiments, the deformable light guide 36 may be provided in a concave shape suitable for conforming to a different tissue, a planar shape, or an irregular shape (which could be a varying shape of any type). In various embodiments, the light source 34 and the deformable light guide 36 are configured to impinge light on various portions of the oral cavity 10 to induce a biological effect within the oral cavity 10, the nasal cavity 12, or both. In particular, by impinging light on the palate 18 of the user, and in particular the soft palate 18-2 of the user, light may penetrate the palate 18 into the nasal cavity 12. In certain embodiments, the light source 34 and the deformable light guide 36 may be configured to impinge light on the palate 18 such that it irradiates the nasopharynx 14, the oropharynx 16, or both. To impinge light on a target tissue area such as the nasopharynx 14 and the oropharynx 16, the number of light sources 34, the arrangement, location, and/or orientation of the light sources 34, the type of light sources 34 (e.g., the light output characteristics of the light source 34 such as peak wavelength, intensity (e.g., radiant flux), polarization (including circular, linear, non-polarized) or the like), the size of the deformable light guide 36, the index of refraction of the deformable light guide 36, the location and/or orientation of the deformable light guide 36 in the housing 32, or the like may be modified to concentrate light towards the tissue area.

The illumination device 30 may be operated by a user. In some embodiments, the illumination device 30 may be configured to turn on automatically when placed in the oral cavity 10 and provide illumination for a desired exposure time to achieve a certain dose. In other embodiments, the illumination device 30 may include button(s) or any other suitable controls for enabling a user to turn the device on and off. In still other embodiments, the illumination device 30 may be controlled wirelessly, for example, from a smartphone or other device. The illumination device 30 may include a haptic engine to provide feedback to a user when starting and/or stopping a treatment protocol.

As discussed above the illumination device 30 is configured to irradiate light into the nasal cavity 12 via the oral cavity 10. In particular, the illumination device 30 is configured to direct light towards separating tissue between the oral cavity 10 and the nasal cavity 12, which in the example above is the palate 18. However, the principles of the present disclosure are not limited to the oral cavity 10 and the nasal cavity 12. In general, the present disclosure contemplates irradiating light into an ancillary body cavity via a primary body cavity. In particular, light may be irradiated onto separating tissue between the primary body cavity and the ancillary body cavity such that light is irradiated through the separating tissue and into the ancillary body cavity. In some cases, the ancillary body cavity may be inaccessible, difficult to access, or induce discomfort when accessed. By irradiating light into the ancillary body cavity via the primary body cavity, a desired dose of light may be provided with minimal invasiveness and discomfort. In addition to irradiating light into the nasal cavity 12 via the oral cavity 10, the principles of the present disclosure may further extend to irradiating light into the cranial cavity via the oral cavity 10, or otherwise irradiating light into any body cavity via any other body cavity.

Those skilled in the art will appreciate that the peak wavelength of light will affect the depth to which the light penetrates into tissue. For example, light having a peak wavelength around 450 nm will be absorbed near the surface of the tissue, while light having a peak wavelength around 850 nm will penetrate deeper into the tissue. In certain embodiments, a depth of a target tissue from a primary emission surface of the illumination device 30 may determine the peak wavelength of the light emitted in order to provide a desired dose to the target tissue. In embodiments herein where a first target tissue and a second target tissue are simultaneously treated by the illumination device 30, the peak wavelength of the light source targeting the first target tissue and the second target tissue may be determined based on the depth of the respective target tissues from the light source.

Figure 3:
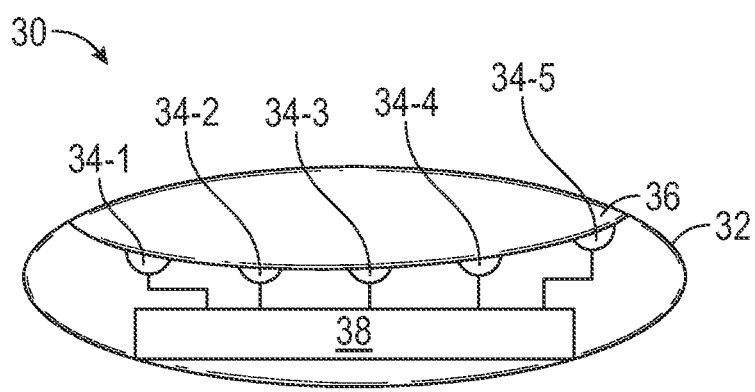
FIG. 3 is a cross-sectional view of an illumination device according to one embodiment of the preset disclosure.

FIG. 3 shows a cross-sectional view of the illumination device 30 according to one embodiment of the present disclosure. Notably, FIG. 3 shows support circuitry 38 in the housing 32. The support circuitry 38 is coupled to each one of the light sources 34 and is configured to provide drive signals to each one of the light sources 34 to cause the light sources 34 to provide light having one or more desired light output characteristics. Accordingly, the support circuitry 38 may include driver circuitry for providing said drive signals. In addition, the support circuitry 38 may include control circuitry for controlling the operation of the illumination device 30, communications circuitry for communicating with devices external to the illumination device 30, power management circuitry for providing power from a power source and/or controlling the charging of a power source, and sensor circuitry for measuring the operation of the illumination device 30. Details of the support circuitry 38 are discussed below. In general, the present disclosure contemplates the complete or partial inclusion of the circuitry necessary to operate the illumination device 30 within the housing 32 thereof. While not shown, a power source such as a battery may be included in the housing 32, or the illumination device 30 may be powered externally (e.g., inductively).

Figure 4A:
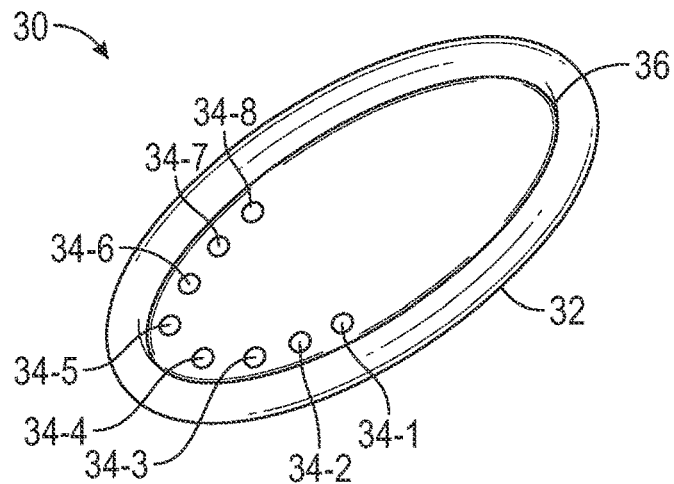
FIGS. 4A through 4C are isometric views of an illumination device according to various embodiments of the present disclosure.
Figure 4B:
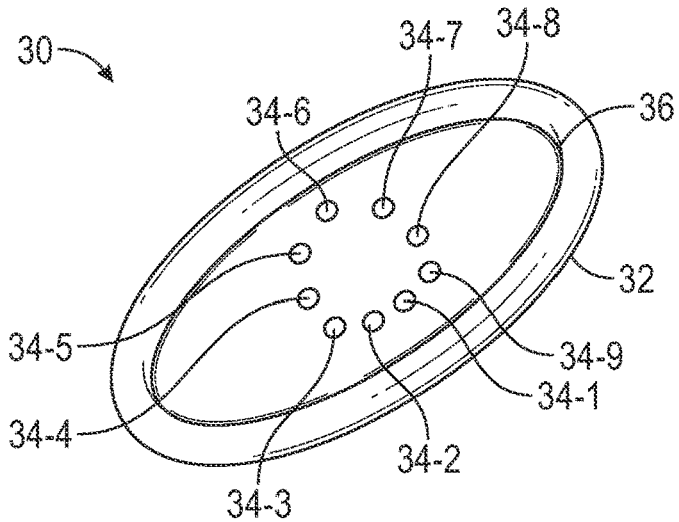
Figure 4C:
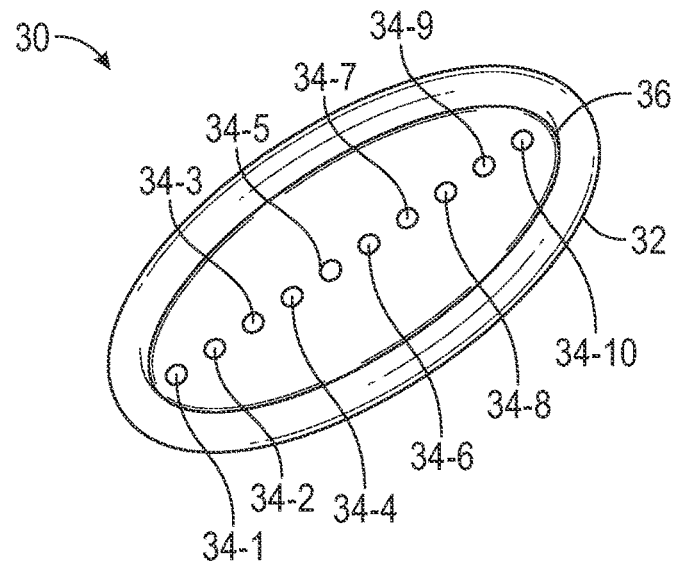

As discussed above, the number of light sources 34 and the arrangement, location, and/or orientation of the light sources 34 may be tailored to direct light toward a particular target tissue. FIGS. 4A through 4C thus show different configurations for the light sources 34 for impinging light on different portions of the oral cavity 10 and thus, in some situations, the nasal cavity 12 as well. In FIG. 4A, the light sources 34 are arranged towards a front of the illumination device 30 such that when the illumination device 30 is provided in the oral cavity 10 the light sources 34 are configured to impinge light on the anterior portion of the palate behind the upper teeth. In FIG. 4B, the light sources 34 are arranged towards a central portion of the illumination device 30 such that when the illumination device 30 is provided in the oral cavity 10 the light sources 34 are configured to impinge light on a central portion of the palate 18. In FIG. 4C, the light sources 34 are arranged along a central line of the illumination device 30 such that when the illumination device 30 is provided in the oral cavity 10 the light sources 34 are configured to impinge light along a central line of the palate 18. Notably, the configurations shown in FIGS. 4A through 4C are merely exemplary and serve to illustrate the fact that the light sources 34 may be provided in any number of different configurations for impinging light on a target tissue area. While the deformable light guide 36 is shown having roughly the same size and shape in FIGS. 4A through 4C, the size and shape of the deformable light guide 36 may be changed along with the configuration of the light sources 34 in order to direct light towards a target tissue area. Further, any of the configurations shown in FIGS. 4A through 4C may be used together.

The illumination device 30 may be configured to be held against the roof of the mouth by the tongue 24. Pressing the illumination device 30 against the roof of the mouth with the tongue 24 may increase the size of the opening into the throat or otherwise alter the tissue exposed in the throat. In some embodiments, the illumination device 30 may be designed such that the active pressing of the illumination device 30 against the roof of the mouth via the tongue exposes a desired tissue within the throat such as the oropharynx 16 in order for the tissue to be irradiated with light.

Figure 5:
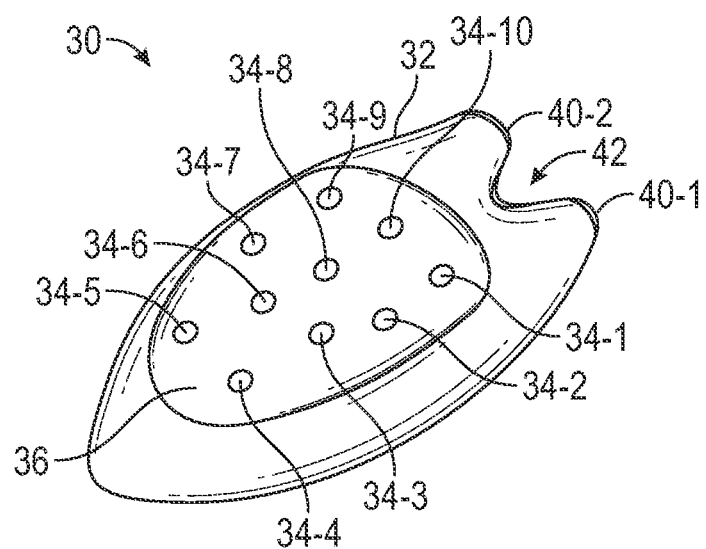
FIG. 5 is an isometric view of an illumination device according to one embodiment of the present disclosure.

FIG. 5 shows the illumination device 30 according to an additional embodiment of the present disclosure. The illumination device 30 shown in FIG. 5 is substantially similar to that shown in FIG. 3 above, except that the illumination device 30 includes a number of ancillary light sources 40 (shown individually as 40-1 and 40-2) and a contoured cutout 42 for targeting tissue at or near the throat of a user. As discussed above, the active pressing of the illumination device 30 into the roof of the mouth by the user may change the size and/or shape of the opening into the throat, thus improving exposure of some tissue for irradiation with light. The ancillary light sources 40 may be configured to be pointed towards the rear of the oral cavity 10 to impinge light onto this target tissue. The contoured cutout 42 may provide space for the uvula 20 while avoiding a gag reflex from the user, thereby allowing the ancillary light sources 40 to extend further into the throat for more direct light exposure onto a target tissue.

As discussed above, while the ancillary light source 40 is shown directed towards the back of the throat, any number of ancillary light sources 40 may be provided in any arrangement, location, or orientation to target different areas of the oral cavity 10 and/or nasal cavity 12. In one embodiment, a number of light sources are arranged to impinge light on one or more salivary glands of a user.

Figure 6:
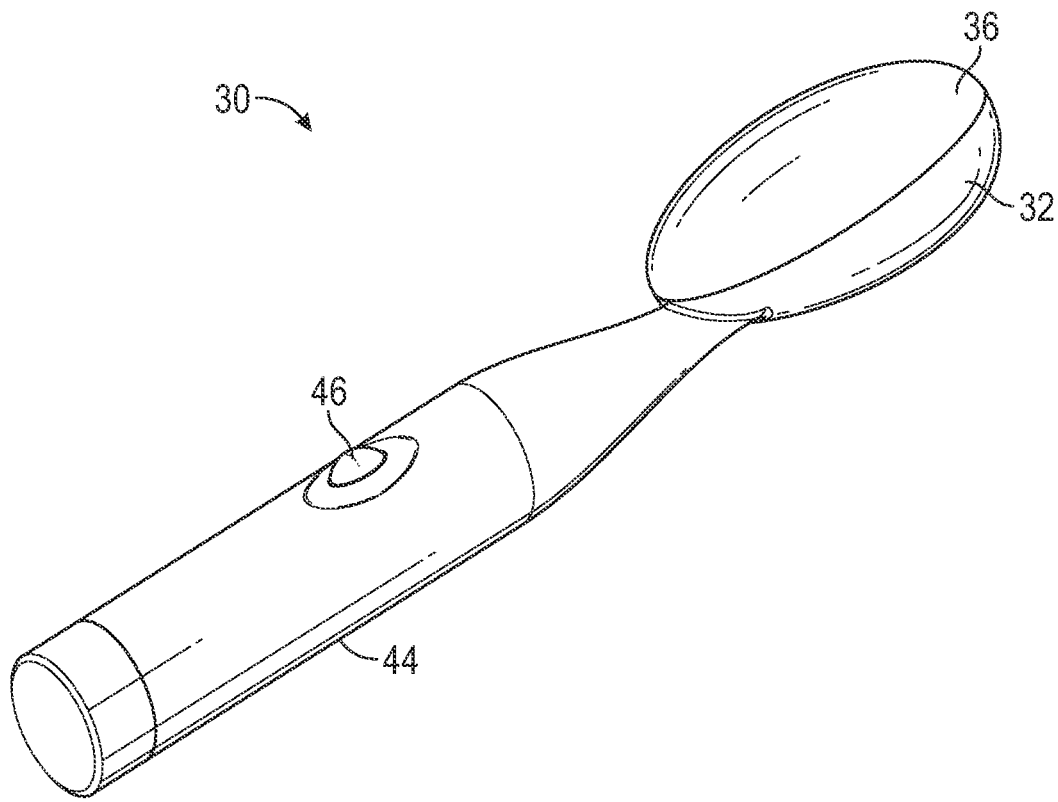
FIG. 6 is an isometric view of an illumination device according to one embodiment of the present disclosure.

FIG. 6 shows the illumination device 30 according to an additional embodiment of the present disclosure. The illumination device 30 shown in FIG. 6 is substantially similar to that shown in FIG. 3, but further includes a handle 44, which is attached to the housing 32 for allowing a user to hold the illumination device 30 and insert it into a body cavity such as the oral cavity 10. The handle 44 may include a button 46 for controlling the operation of the illumination device 30, or any other controls. While the light source 34 is shown inside the housing 32 above, the light source 34 may also be provided external to the housing 32 in the handle 44 in some embodiments. In these embodiments, light may be coupled into the deformable light guide 36 via an additional portion of the deformable light guide 36, an additional light guide, or any other suitable optical component. Further, all or a portion of the support circuitry 38 may be located in the handle 44.

The housing 32 may comprise any material suitable for being provided completely or partially within a body cavity. In various embodiments, the housing 32 may comprise or be coated with a biocompatible material of some kind. The light sources 34 may comprise any suitable light source capable of emitting light that may induce one or more of the aforementioned biological effects, including but not limited to light emitting diodes (LEDs), organic light emitting diodes (OLEDs), superluminescent diodes (SLDs), lasers, and/or any combinations thereof. Where a light source 34 is described as emitting light of a wavelength or a range of wavelengths, it should be understood that the term wavelength could refer to a dominant wavelength or a peak wavelength. Unless otherwise specified, various embodiments are provided herein with reference to peak wavelengths. While a certain number of light sources 34 are shown in the embodiments discussed herein, any number of light sources 34 may be used in an illumination device 30 according to the present disclosure. The deformable light guide 36 may comprise any deformable material that is capable of conforming to a target tissue area and having one or more desired optical characteristics such as refractivity index. In one embodiment, the deformable light guide 36 comprises silicone. However, any material with the aforementioned desired characteristics may be used. In one embodiment, an index of refraction of the deformable light guide is no greater than 0.15 an index of refraction of water. In certain embodiments, the deformable light guide 36 may comprise a liquid or gel coating on the light source 34, rather than a deformable solid. This could be useful not only when the illumination device 30 is provided within a body cavity of a user, but also when the illumination device 30 is used outside of the body as well.

While the housing 32 of the illumination device 30 is shown having an ovoid shape in the exemplary embodiments above, the housing 32 may be provided in any shape without departing from the principles of the present disclosure. The shape of the housing 32 may be adapted to a particular body cavity in which it is to be partially or completely provided. While the deformable light guide 36 is shown in a convex shape that is adapted to conform easily to the roof of the mouth, the deformable light guide 36 may be provided in any suitable shape for conforming to a target tissue area without departing from the principles discussed herein.

Figure 7:
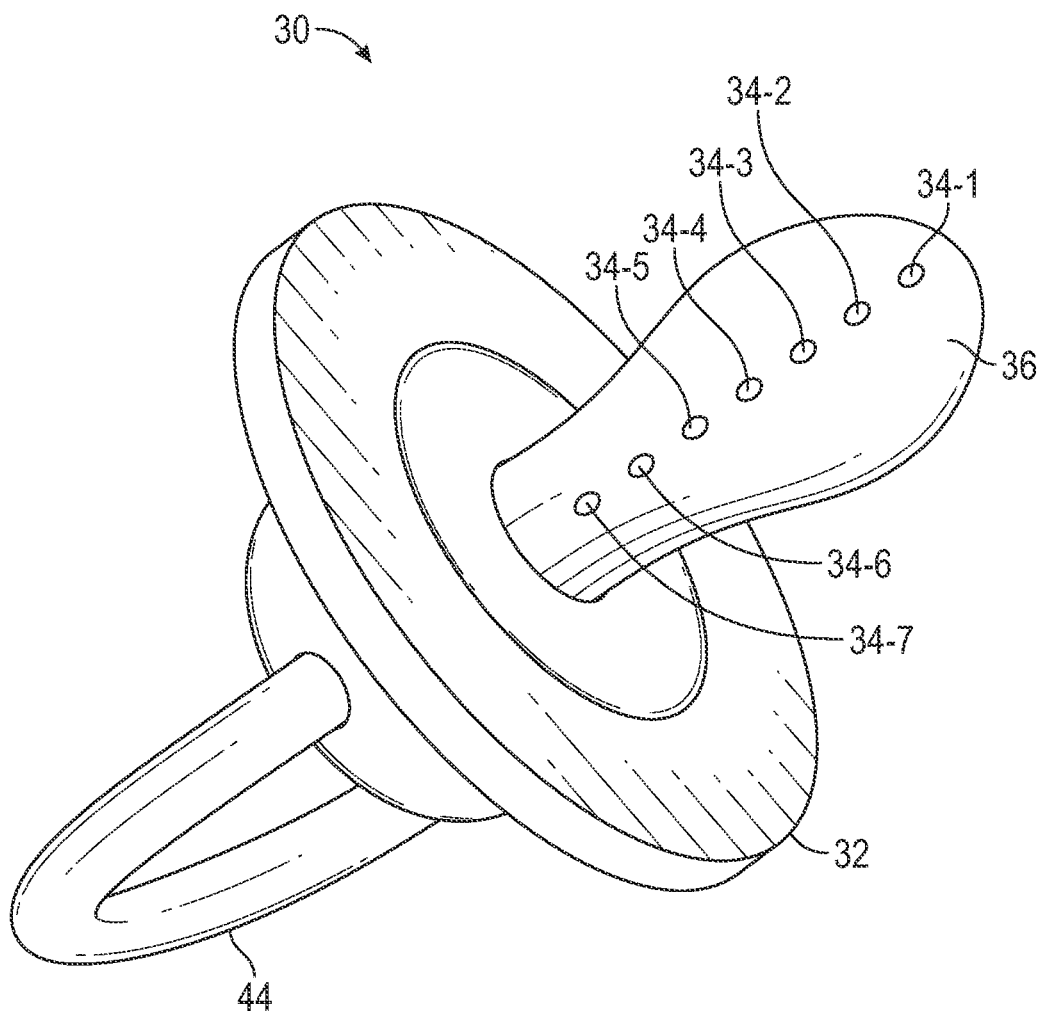
FIG. 7 is an isometric view of an illumination device according to one embodiment of the present disclosure.

FIG. 7 shows the illumination device 30 according to an additional embodiment of the present disclosure. As shown, the illumination device 30 is provided in a pacifier form, wherein the deformable light guide 36 provides a bulbous shape configured to be provided comfortably within the oral cavity 10. The light source 34 is within the deformable light guide 36 or otherwise optically coupled thereto so that light is coupled from the deformable light guide 36 into the oral cavity 10 when in use. The housing 32 includes a flanged portion configured to rest against the lips when in use to hold a portion of the illumination device 30 outside the oral cavity 10. The handle 44 may be a ring attached to the housing 32. Notably, the shapes of the illumination device 30 shown herein are merely exemplary. Pacifiers are often considered therapeutic for children and are even used in adults to provide relief for certain medical conditions such as depression, drug addiction, sleeping disorders, anxiety, and the like. Providing the illumination device 30 in such a shape may allow for additional benefits such as the biological effects discussed above. Those skilled in the art will appreciate that the illumination device may be provided in any number of shapes and sizes without departing from the principles herein.

Figure 8:
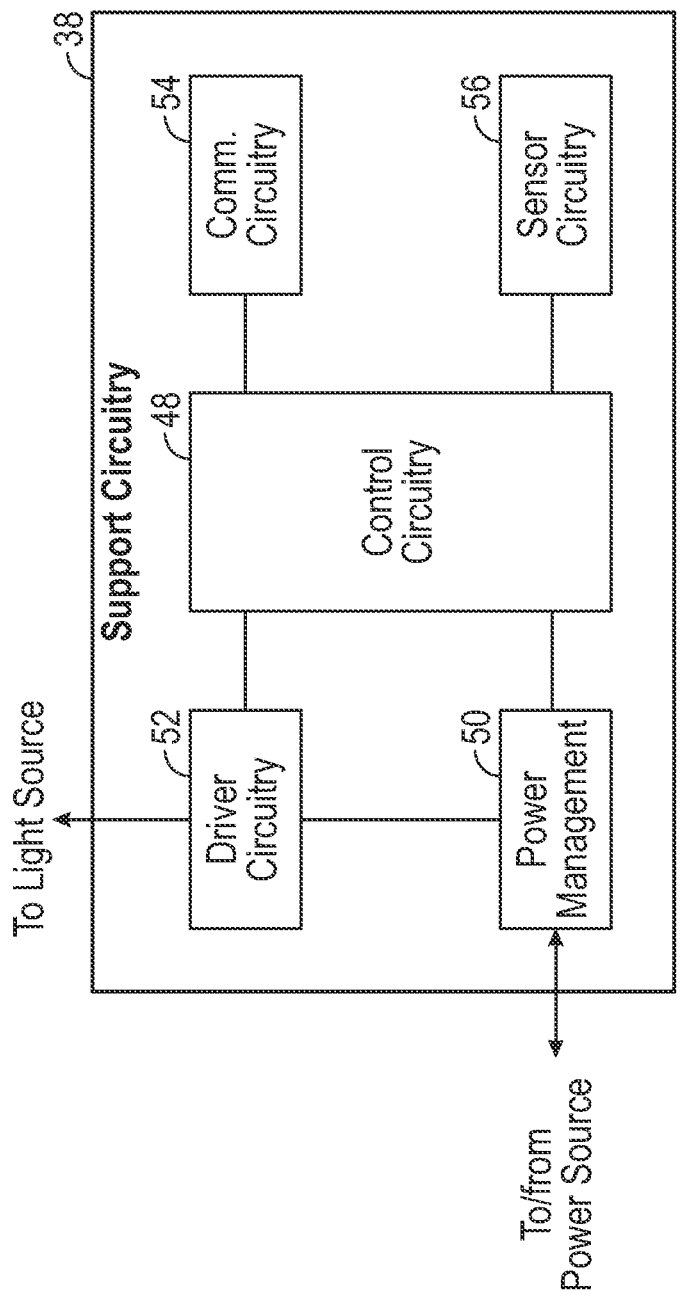
FIG. 8 is a block diagram showing details of supporting circuitry according to one embodiment of the present disclosure.

FIG. 8 is a block diagram illustrating support circuitry 38 according to one embodiment of the present disclosure. The support circuitry 38 may include control circuitry 48, which may include a processor and/or memory for controlling the operation of the illumination device. The support circuitry 38 may further include power management circuitry 50 coupled to the control circuitry 48 and configured to control the charging of and/or consumption of power from a power source. The support circuitry 38 may further include driver circuitry 52 for generating drive signals for the light sources 34. The drive signals may be direct current (DC) signals, or alternating signals such as alternating current (AC) signals, pulse width modulated (PWM) signals, or any other suitable signals. The support circuitry 38 may include communications circuitry 54 configured to allow the illumination device 30 to communicate with one or more other devices. Finally, the support circuitry 38 may include sensor circuitry 56, which may include any number of sensors (e.g., light sensors, temperature sensors) for monitoring the operation of the illumination device 30. Notably, the exemplary components of the support circuitry 38 are neither required nor exhaustive.

Figure 9:
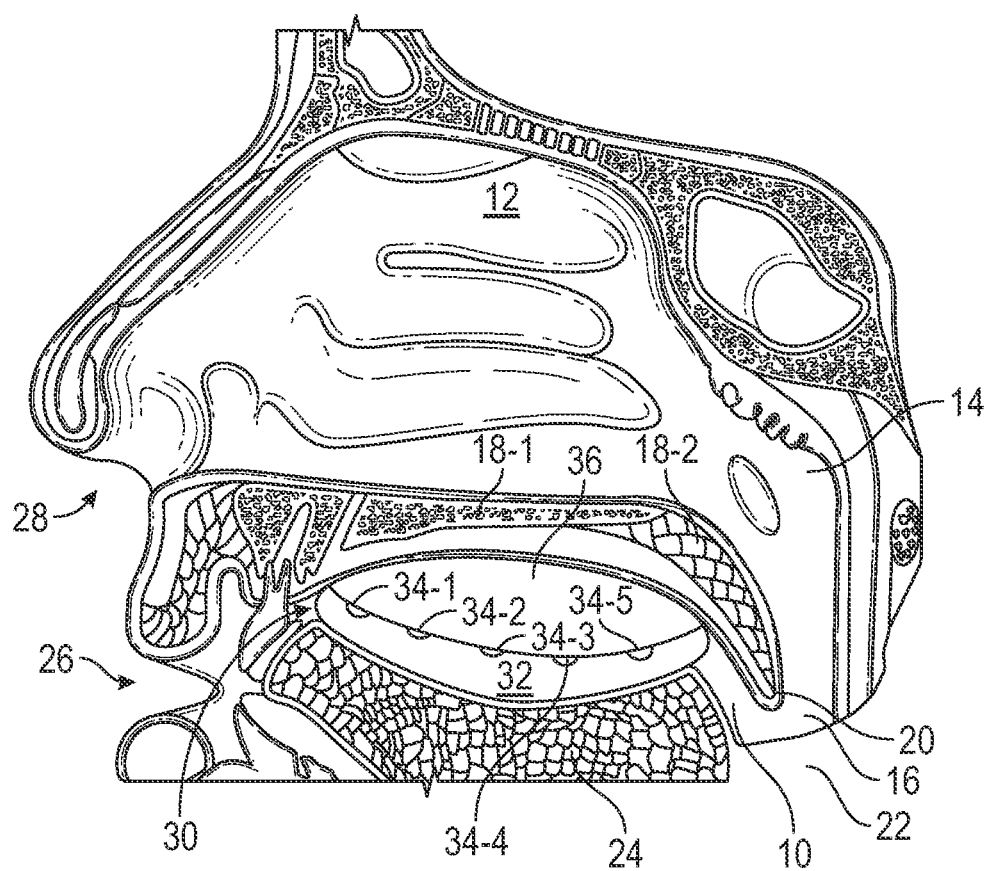
FIG. 9 is a cross-sectional view of a nasal cavity and an oral cavity including an illumination device according to one embodiment of the present disclosure.

FIG. 9 shows the same cross-section of the oral cavity 10 and the nasal cavity 12 as in FIG. 1, with the illumination device 30 inserted into the oral cavity 10. As shown, the illumination device 30 is held against the roof of the mouth by the tongue 24 such that the deformable light guide 36 conforms to the roof of the mouth in order to directly couple light into the palate 18. This may allow for better light coupling into the palate 18 and thus through to the nasal cavity 12, reaching the nasopharynx 14 in some embodiments.

Figure 10:
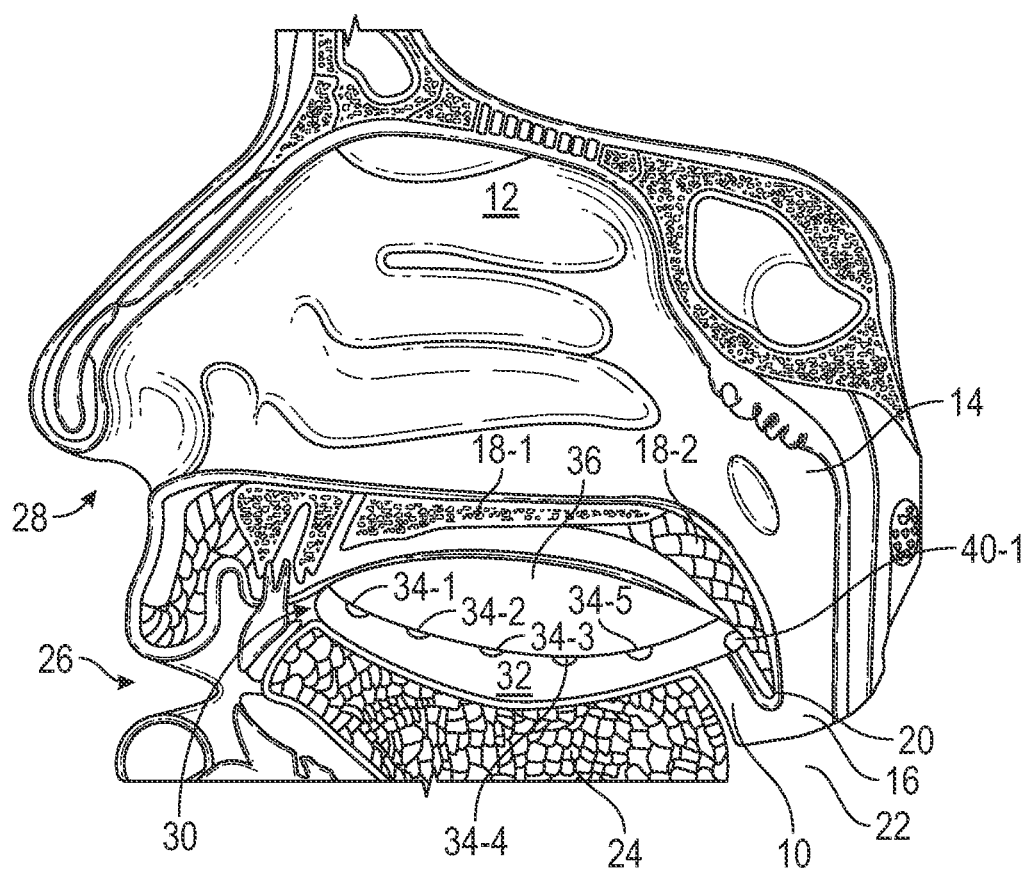
FIG. 10 is a cross-sectional view of a nasal cavity and an oral cavity including an illumination device according to one embodiment of the present disclosure.

FIG. 10 shows the same cross-section of the oral cavity 10 and the nasal cavity 12 as in FIG. 9, but the illumination device 30 further includes the contoured cutout 42 and the ancillary light source 40, which further extends into the opening at the back of the mouth to provide light to target tissues at the back of the throat such as the oropharynx 16.

Figure 11:
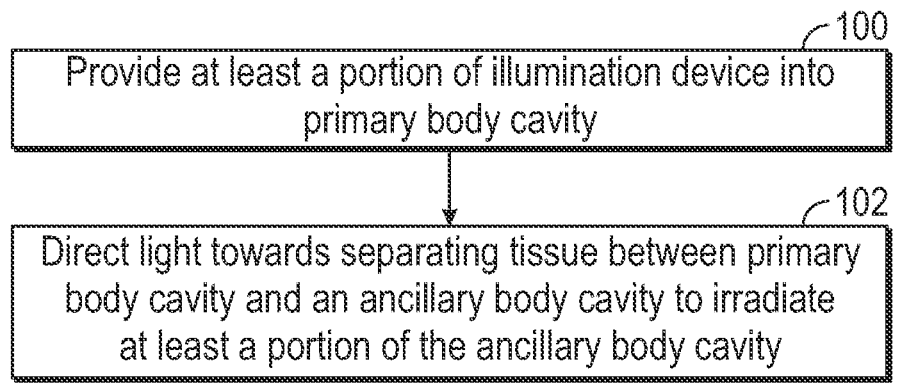
FIG. 11 is a flow diagram illustrating a method of irradiating light into a body cavity according to one embodiment of the present disclosure.

As discussed above, the principles of the present disclosure generally contemplate irradiating light into one body cavity from a different body cavity. FIG. 11 is thus a flow diagram illustrating a method for administering light into a body cavity of a user according to one embodiment of the present disclosure. First, at least a portion of an illumination device is provided into a primary body cavity of a user (step 100). As discussed above, this could be the oral cavity 10 of a user, but it could also be any other body cavity. Light is then directed towards separating tissue between the primary body cavity and an ancillary body cavity to irradiate at least a portion of the ancillary body cavity with light (step 102). As discussed above, the ancillary body cavity could be the nasal cavity 12 and the separating tissue could be the palate 18. However, the principles of the present disclosure apply equally to any ancillary body cavity and any separating tissue. In some embodiments, the ancillary body cavity may be separated from the primary body cavity by more than one separating tissue. In these embodiments, the light must irradiate all of the separating tissue to enter the ancillary body cavity, and thus the light provided by the light source 34 may be adjusted accordingly (e.g., by altering the peak wavelength, intensity, polarization, and/or duration).

For any of the embodiments discussed herein, the light source 34 may be functionally separated into a first light source and a second light source. The first light source and the second light source may each include any number of individual light sources. The functional separation between the light sources is the fact that the first light source provides light having one or more first light output characteristics while the second light source provides light having one or more second light output characteristics. The light output characteristics could include peak wavelength, intensity (e.g., radiant flux), polarization, and duration of exposure (e.g., via different modulation), or any other light output characteristic. In various embodiments, the arrangement, location, and/or orientation of the first light source may be configured to irradiate light onto a first target tissue area, while the arrangement, location, and/or orientation of the second light source may be configured to irradiate light onto a second target tissue area. The first target tissue area and the second target tissue area may be located in the same body cavity of the user, or in different body cavities of the user. In particular, the first target tissue area may be in the oral cavity, while the second target tissue area may be in the nasal cavity.

Figure 12:
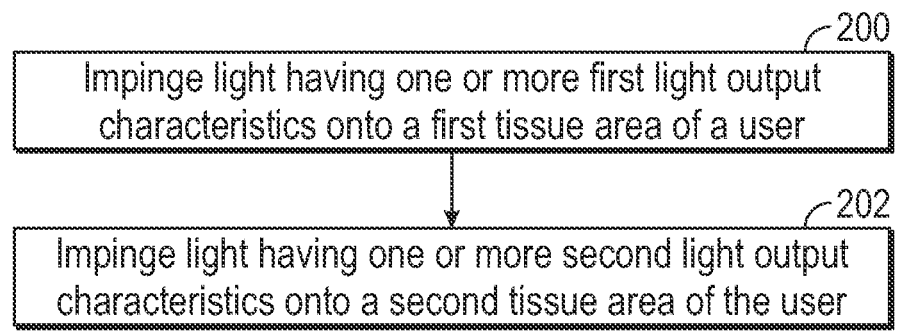
FIG. 12 is a flow diagram illustrating a method for irradiating light onto different tissue areas of a user according to one embodiment of the present disclosure.

FIG. 12 thus shows a flow diagram illustrating a method for illuminating different tissue areas of a user according to one embodiment of the present disclosure. First, light having one or more first light output characteristics is impinged onto a first tissue area of a user (step 200). As discussed above, the light output characteristics may include peak wavelength, intensity (e.g., radiant flux), polarization, and/or duration of exposure (e.g., via different modulation), or any other light output characteristic. Next, light having one or more second light output characteristics is impinged onto a second tissue area of the user (step 202). The first light output characteristics are different from the second light output characteristics. For example, the light impinged on the first tissue area may have a different peak wavelength, intensity (e.g., radiant flux), polarization, and/or duration of exposure than the light impinged on the second tissue area. The light impinged on the first tissue area may be provided from a different light source than the light impinged on the second tissue area. The light impinged on the first tissue area may be provided from the same illumination device 30 as the light impinged on the second tissue area. In some embodiments, the first tissue area is distinct from the second tissue area such that the first tissue area does not overlap with the second tissue area. Further, the first tissue area may be located in a different body cavity from the second tissue area in various embodiments. In some embodiments, the light may be impinged on the first tissue area at the same time the light is impinged on the second tissue area. In other embodiments, the light impinged on the first tissue area and the second tissue area occurs during non-overlapping treatment windows.

While previously described embodiments have been provided in the context of an illumination device 30 configured to impinge light on target tissue of a user, the principles of the present disclosure are also applicable to one or more other types of directed energy sources in addition to the light source 34. As used herein, a directed energy source may include any of the various light sources previously described and/or an energy source capable of providing one or more of heat, IR heating, resistance heating, radio waves, microwaves, sound waves, ultrasound waves, electromagnetic interference, and electromagnetic radiation that may be directed to a target tissue. In certain embodiments, a device may include multiple types of directed energy sources including a light source and another type of directed energy source.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. An illumination device comprising:
   a housing;
   a light source within the housing;
   support circuitry within the housing, the support circuitry being coupled to the light source;
   a deformable light guide on the housing and optically coupled to the light source, the deformable light guide configured to conform to a surface of tissue when in contact with the tissue such that light from the light source is coupled directly from the deformable light guide to the tissue; and
   an additional light source positioned within the housing such that light from the additional light source exits a portion of the housing that is separate from the deformable light guide.

2. The illumination device of claim 1 wherein the tissue is located within a body cavity of a user.

3. The illumination device of claim 2 wherein the light source is configured to be positioned outside the body cavity during use of the illumination device.

4. The illumination device of claim 2 wherein the light source is configured to be positioned inside the body cavity during use of the illumination device.

5. The illumination device of claim 2 wherein the tissue is located within an oral cavity of the user.

6. The illumination device of claim 5 wherein the deformable light guide is configured to conform to the roof of the mouth of the user.

7. The illumination device of claim 6 wherein the deformable light guide provides a convex surface for interfacing with the roof of the mouth of the user.

8. The illumination device of claim 7 wherein the deformable light guide and the light source are configured to irradiate light into the nasal cavity of the user via the palate of the user.

9. The illumination device of claim 8 wherein a primary emission surface of the deformable light guide is oriented in a direction toward the palate of the user.

10. The illumination device of claim 9 wherein the light from the additional light source is configured to irradiate the throat of the user.

11. The illumination device of claim 8 wherein the deformable light guide and the light source are configured to irradiate light on the nasopharynx of the user.

12. The illumination device of claim 5 wherein the deformable light guide and the light source are configured to irradiate light on one or more salivary glands of the user.

13. The illumination device of claim 1 wherein a primary emission surface of the deformable light guide is oriented in a direction of the tissue.

14. The illumination device of claim 1 wherein the deformable light guide comprises silicone.

15. The illumination device of claim 1 wherein the deformable light guide comprises an index of refraction that is no greater than 0.15 of an index of refraction of water.

16. The illumination device of claim 1 wherein the light source is configured to provide light with a first peak wavelength that induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

17. The illumination device of claim 16, wherein the first peak wavelength is in a range from one of: 410 nm to 450 nm, 630 nm to 670 nm, 350 nm to 395 nm, 320 nm to 350 nm, 385 nm to 450 nm, 400 nm to 700 nm, and 700 nm to 1000 nm.

18. The illumination device of claim 16, wherein the light source is configured to provide light with a second peak wavelength that is different than the first peak wavelength.

19. The illumination device of claim 1 wherein the deformable light guide comprises a hydrophobic material that is configured to repel mucus.

20. The illumination device of claim 1 wherein the deformable light guide provides at least one of a concave surface, a convex surface, a planar surface, and an irregular surface for interfacing with the tissue.

21. An illumination device comprising:
    a housing;
    a light source within the housing;
    support circuitry within the housing, the support circuitry being coupled to the light source;
    a light guide on the housing and optically coupled to the light source, the light source and the light guide configured to irradiate light into an ancillary body cavity of a user via a primary body cavity of the user; and
    an additional light source positioned within the housing such that light from the additional light source exits the housing adjacent a contoured cutout of the housing that is separate from the light guide.

22. The illumination device of claim 21 wherein:
    the primary body cavity is separated from the ancillary body cavity by separating tissue; and
    the light guide and the light source are configured to direct light emissions towards the separating tissue in order to irradiate light into the ancillary body cavity.

23. The illumination device of claim 22 wherein the primary body cavity is the oral cavity of the user and the ancillary body cavity is the nasal cavity of the user.

24. The illumination device of claim 23 wherein the separating tissue comprises the soft palate of the user.

25. The illumination device of claim 24 wherein a primary emission surface of the light guide is oriented in a direction toward the soft palate of the user.

26. The illumination device of claim 22 wherein a primary emission surface of the light guide is oriented in a direction toward the separating tissue.

27. The illumination device of claim 26 wherein the light guide is a deformable light guide configured to conform to a surface of tissue when in contact with the tissue such that light from the light source is coupled directly from the deformable light guide to the tissue.

28. The illumination device of claim 27 wherein the light guide comprises silicone.

29. The illumination device of claim 27 wherein the light guide comprises an index of refraction that is no greater than 0.15 of an index of refraction of water.

30. The illumination device of claim 21 wherein the primary body cavity is the oral cavity of the user and the ancillary body cavity is the nasal cavity of the user.

31. The illumination device of claim 21 wherein the light source is configured to be positioned outside the primary body cavity during use of the illumination device.

32. The illumination device of claim 21 wherein the light source is configured to be positioned inside the primary body cavity during use of the illumination device.

33. The illumination device of claim 21 wherein the light source is configured to provide light with a first peak wavelength that induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

34. The illumination device of claim 33, wherein the first peak wavelength is in a range from one of: 410 nm to 450 nm, 630 nm to 670 nm, 350 nm to 395 nm, 320 nm to 350 nm, 385 nm to 450 nm, 400 nm to 700 nm, and 700 nm to 1000 nm.

35. The illumination device of claim 33, wherein the light source is configured to provide light with a second peak wavelength that is different than the first peak wavelength.

36. An illumination device comprising:
a housing;
a first light source and a second light source within the housing;
support circuitry within the housing, the support circuitry comprising driver circuitry coupled to the first light source and the second light source, and communications circuitry configured to communicate with one or more devices external to the housing; and
a light guide on the housing and optically coupled to the first light source, wherein:
the light guide and the first light source are configured to irradiate light having one or more first light output characteristics onto a first tissue area of a user; and
the second light source is configured to irradiate light having one or more second light output characteristics onto a second tissue area of a user such that the light of the second light source exits a portion of the housing that is separate from the light guide, and the second tissue area is different from the first tissue area, wherein the one or more first light output characteristics are different from the one or more second light output characteristics.

37. The illumination device of claim 36 wherein the first tissue area is located in a first body cavity of the user and the second tissue area is located in a second body cavity of the user that is different from the first body cavity.

38. The illumination device of claim 37 wherein the first tissue area is located in an oral cavity of the user and the second tissue area is located in the nasal cavity of the user.

39. The illumination device of claim 37 wherein the first body cavity is separated from the second body cavity by separating tissue.

40. The illumination device of claim 39 wherein the light guide is configured such that:
light from the first light source is directed towards the first tissue area; and
light from the second light source is directed towards the separating tissue in order to penetrate the separating tissue and irradiate the second tissue area.

41. The illumination device of claim 40 wherein:
the first tissue area is located in the oral cavity of the user;
the second tissue area is located in the nasal cavity of the user; and
the separating tissue is the palate of the user.

42. The illumination device of claim 41 wherein the one or more first light output characteristics and the one or more second light output characteristics include one or more of peak wavelength, intensity, polarization, and duration of exposure.

43. The illumination device of claim 37 wherein the one or more first light output characteristics and the one or more second light output characteristics include one or more of peak wavelength, intensity, polarization, and duration of exposure.

44. The illumination device of claim 37 wherein:
the first light source is configured to provide light with a first peak wavelength that induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect; and
the second light source is configured to provide light with a second peak wavelength that is different than the first peak wavelength, wherein the second peak wavelength induces at least one biological effect, the at least one biological effect comprising one or more of inactivating microorganisms that are in a cell-free environment, inhibiting replication of microorganisms that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect.

45. The illumination device of claim 44, wherein:
the first peak wavelength is in a range from one of: 410 nm to 450 nm, 630 nm to 670 nm, 350 nm to 395 nm, 320 nm to 350 nm, 385 nm to 450 nm, 400 nm to 700 nm, and 700 nm to 1000 nm; and
the second peak wavelength is in a range from one of: 410 nm to 450 nm, 630 nm to 670 nm, 350 nm to 395 nm, 320 nm to 350 nm, 385 nm to 450 nm, 400 nm to 700 nm, and 700 nm to 1000 nm.

* * * * *